United States Patent [19]
Tanabe et al.

[11] Patent Number: 5,306,688
[45] Date of Patent: Apr. 26, 1994

[54] SALICYLIC ACID DERIVATIVES, THE PROCESS FOR PREPARING THE SAME AND THE HEAT-SENSITIVE RECORDING MATERIALS COMPRISING THEREOF

[75] Inventors: Yoshimitsu Tanabe, Yokohama; Yuki Kobayashi, Kamakura; Atsuo Otsuji, Yokohama; Masakatsu Nakatsuka, Yokohama; Kiyoharu Hasegawa, Yokohama; Kazuyoshi Kikkawa; Akihiro Yamaguchi, both of Kamakura; Naomasa Koike; Fumio Okumura, both of Tokyo, all of Japan

[73] Assignees: Mitsui Toatsu Chemicals, Inc.; Mitsubishi Paper Mills Limited, both of Tokyo, Japan

[21] Appl. No.: 946,694

[22] Filed: Sep. 18, 1992

[30] Foreign Application Priority Data

Sep. 24, 1991 [JP] Japan .................. 3-243201
Jun. 26, 1992 [JP] Japan .................. 4-168744

[51] Int. Cl.$^5$ ............................................. B41M 5/32
[52] U.S. Cl. ................................... 503/210; 427/150; 503/211; 503/212; 503/216; 503/225
[58] Field of Search .................. 427/150-152; 503/210-212, 216, 218, 225

[56] References Cited
FOREIGN PATENT DOCUMENTS 0253666 1/1988 European Pat. Off. .......... 503/216
263037 11/1949 Switzerland ................ 503/216

Primary Examiner—B. Hamilton Hess
Attorney, Agent, or Firm—Millen, White, Zelano & Branigan

[57] ABSTRACT

A heat-sensitive recording material comprising a color forming, electron donating compound and a salicylic acid derivative represented by the formula (1):

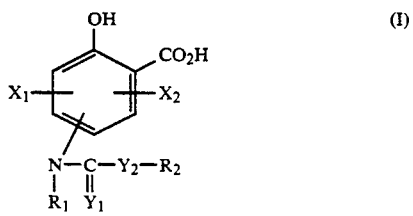

wherein $X_1$ and $X_2$ are a hydrogen atom, an alkyl group, an alkoxy group, an aralkyl group, an aryl group or a halogen atom, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group, and/or a metal salt of the salicylic acid derivative as an electron accepting compound, is disclosed.

12 Claims, 2 Drawing Sheets

SALICYLIC ACID DERIVATIVES, THE PROCESS FOR PREPARING THE SAME AND THE HEAT-SENSITIVE RECORDING MATERIALS COMPRISING THEREOF

BACKGROUND OF THE INVENTION

1. Field of the Invention

The present invention relates to a heat-sensitive recording material and particularly relates to a heat-sensitive recording material having improved storage stability of an uncolored portion and a developed color image. Further, the invention relates to metal salts of salicylic acid derivatives which are useful as an electron accepting compound in the heat-sensitive recording material and a process for preparing said salicylic acid derivatives and metal salts of the same.

2. Related Art of the Invention

Heat-sensitive recording materials which utilize color forming reaction of electron donating compounds with electron accepting compounds(developer) have conventionally been well known, for example, in Japanese Patent Publication Sho 43-4160 and 45-14039.

Heat-sensitive recording materials are relatively inexpensive and advantageous in that recording equipment is compact and free from maintenance, and hence have widely been used in the field of a facsimile, recorder and printer.

Recently, use field of heat-sensitive recording materials has been further extended and diversified to uses under severe environment, for example, labels and prepaid cards.

However, conventionally known heat-sensitive recording materials which employ 2,2-bis(4'-hydroxyphenyl)propane(bisphenol A) or benzyl 4-hydroxybenzoate as an electron accepting compound have such a disadvantage that remarkable soiling of an uncolored portion or fading of a developed color image occurs in the severe environment, for example, in contact with oils, solvents, fats and writing utensils such as a fluorescent pen or in moist environment.

In order to improve these disadvantages, heat-sensitive recording materials which contain salicylic acid derivatives having substituted amino groups or metal salts thereof as electron accepting compounds have been proposed (Japanese Laid-Open Patent Sho 63-95979).

However, the heat-sensitive recording material which uses 4-phenylacetylaminosalicylic acid or a metal salt such as zinc salt of the same which described in the patent as an electron accepting compound is still poor in the storage stability of a developed color image against moist heat, has low sensitivity for color development and cannot conform to practical high-speed recording. The heat-sensitive recording material obtained as described in the patent by using 4-benzoylaminosalicylic acid and metal salts(for example, zinc salt) thereof as an electron accepting compound has also poor storage stability, for example, moist heat resistance of a developed color image and a disadvantage of low developing sensitivity. Further, the heat-sensitive recording material obtained by using a similar compound 4-n-octylcarbonylaminosalicylic acid or its metal salts such as zinc salt as an electron accepting compound has also the same disadvantages as above. On the basis of such circumstances, it has been strongly desired to develop a heat-sensitive recording material having good developing sensitivity and further improved storage stability of the uncolored portion and developed color image.

Relatively many salicylic acid derivatives having an amino group have been known to be used for heat-sensitive recording materials as disclosed above.

The salicylic acid derivative which is disclosed in the invention has a carbamate group as a substituent and is represented by the formula (1). Some of the salicylic acid derivative represented by the formula (1) have already been prepared, for example, in German Patent 2749518, Bull. de Socie. Chim. France, 1189 (1955), and J. Pharm. Sci., 52, 927 (1963). The sodium salt of the salicylic acid derivative is the only metal salt which has been disclosed and no disclosure has been found at all on divalent, trivalent and tetravalent metal salts. As to the application to the heat-sensitive recording material, no disclosure has been found on the salicylic acid derivative having the carbamate group as a substituent or a metal salt of the derivative.

The above German Patent 2749518 has disclosed a preparation process of 4-benzyloxycarbonylaminosalicylic acid and 5-benzyloxycarbonylaminosalicylic acid by individually reacting 4-aminosalicylic acid and 5-aminosalicylic acid with benzylchloroformate in dry pyridine. However, the yield is very low. For example, the yield of 5-benzyloxycarbonylaminosalicylic acid in the process is about 25%.

In the preparation process described in Bull. de Socie. Chim. France, 1189 (1955), 4-alkyloxycarbonylaminosalicylic acid is obtained by reacting an aqueous sodium 4-aminosalicylate solution with alkylchloroformate. However, the yield is not satisfactory in the process. For example, the yield of 4-n-pentyloxycarbonylaminosalicylic acid is about 70%.

In the preparation process described in J. Pharm. Sci., 52, 927 (1963), 4-aminosalicylic acid and 5-aminosalicylic acid is reacted with phenylchloroformate in an aqueous sodium hydrogen carbonate solution to obtain 4-phenyloxycarbonylaminosalicylic acid and 5-phenyloxycarbonylaminosalicylic acid, respectively, in the relatively high yield.

However, the present inventors have found that, when 4-aminosalicylic acid or 5-aminosalicylic acid is reacted in an aqueous sodium hydrogen carbonate solution with various chloroformate compounds, particularly alkylchloroformate compounds having more than 5 carbon atoms, the yield of desired 4-carbamate substituted salicylic acid derivative or 5-carbamate substituted salicylic acid derivative is very low (50% or less).

Consequently, it has been strongly desired to develop a simple and broadly applicable process for preparing a carbamate substituted salicylic acid derivative in high purity.

OBJECTS OF THE INVENTION

The object of the invention is to provide a heat-sensitive recording material having remarkably improved storage stability of an uncolored portion and a developed color image.

The second object of the invention is to provide a divalent, trivalent or tetravalent metal salt of a salicylic acid derivative which is useful as an electron accepting compound of said heat-sensitive recording material.

The third object of the invention is to provide a process for preparing the salicylic acid derivative and the metal salt of the derivative.

In order to achieve the above objects, the present inventors have carried out an intensive investigation on the heat-sensitive recording material, the electron accepting compound in particular, and completed the invention.

SUMMARY OF THE INVENTION

The present invention is a heat-sensitive recording material comprising a color forming, electron donating compound and an electron accepting compound wherein said electron accepting compound is one or more compound selected from a salicylic acid derivative represented by the formula (1):

(1)

wherein $X_1$ and $X_2$ each are a hydrogen atom, an alkyl group, an alkoxy group, an aralkyl group, an aryl group or a halogen atom, $Y_1$ and $Y_2$ each are an oxygen or a sulfur atom, $R_1$ is a hydrogen atom, an alkyl group, an aralkyl group or an aryl group, and $R_2$ is an alkyl group, an alkenyl group, an aralkyl group or an aryl group, and/or a metal salt of said salicylic acid derivative; a divalent, trivalent or tetravalent metal salt of the salicylic acid derivative represented by the formula (1); a process for preparing the salicylic acid derivative represented by the formula (1) by reacting a compound represented by the formula (2):

(2)

wherein X, and $X_2$ are a hydrogen atom, an alkyl group, an alkoxy group, an aralkyl group, an aryl group or a halogen atom, and $R_1$ is a hydrogen atom, an alkyl group, an aralkyl group or an aryl group, with a compound represented by the formula (3):

(3)

wherein $Y_1$ and $Y_2$ are an oxygen atom or a sulfur atom, $R_2$ is an alkyl group, an alkenyl group, an aralkyl group or an aryl group, and Z is a halogen atom, in the presence of an alcohol-based solvent; and a process for preparing a multivalent metal salt of salicylic acid derivative by reacting said salicylic acid derivative with a salt of from divalent to tetravalent metal.

The invention provides a heat-sensitive recording material whose uncolored portions have excellent storage stability and a developed color image and has enhanced developing sensitivity.

DETAILED DESCRIPTION OF THE INVENTION

The present invention is a heat-sensitive recording material comprising a color forming, electron donating compound and an electron accepting compound wherein said electron accepting compound is a salicylic acid derivative represented by the formula (1) and/or a metal salt of the salicylic acid derivative.

The salicylic acid derivative and the metal salt of the derivative which can be used in the invention have following atoms and groups in the formula (1).

$X_1$ and $X_2$ are a hydrogen or halogen atom, an alkyl, alkoxy, aralkyl or aryl group, preferably hydrogen, $C_1 \sim C_{20}$ alkyl, $C_5 \sim C_{14}$ alicyclic, $C_1 \sim C_{20}$ alkoxy, $C_7 \sim C_{20}$ aralkyl, phenyl, fluorine, chlorine or bromine, more preferably hydrogen, $C_1 \sim C_4$ alkyl, cyclohexyl, $C_1 \sim C_4$ alkoxy, benzyl, α-methylbenzyl, cumyl, phenyl or chlorine, and most preferably hydrogen.

$Y_1$ and $Y_2$ are a oxygen or sulfur atom, and preferably $Y_1$ is oxygen.

$R_1$ is a hydrogen atom, an alkyl, aralkyl or aryl group, preferably hydrogen, $C_1 \sim C_{20}$ alkyl, $C_5 \sim C_{14}$ alicyclic, $C_7 \sim C_{20}$ aralkyl, phenyl or substituted phenyl, more preferably hydrogen, $C_1 \sim C_8$ alkyl, cyclopentyl, cyclohexyl, cycloheptyl, benzyl or phenyl, further preferably hydrogen, $C_1 \sim C_4$ alkyl or phenyl, and most preferably hydrogen.

$R_2$ is an alkyl, alkenyl, aralkyl or aryl group, preferably alkyl or substituted alkyl, alicyclic or substituted alicyclic, alkenyl or substituted alkenyl, cyclic alkenyl or substituted cyclic alkenyl, aralkyl or substituted aralkyl, phenyl or substituted phenyl, naphthyl or substituted naphthyl, or heteroaromatic or substituted heteroaromatic.

The alkyl or alkenyl represented by $R_2$ can be monosubstituted or polysubstituted.

The substituents include, for example, $C_1 \sim C_{20}$ alkoxy, $C_2 \sim C_{20}$ alkoxyalkyloxy, $C_2 \sim C_{20}$ alkenyloxy, $C_7 \sim C_{20}$ aralkyloxy, $C_8 \sim C_{20}$ aralkyloxyalkoxy, $C_6 \sim C_{20}$ aryloxy, $C_7 \sim C_{20}$ aryloxyalkoxy, $C_8 \sim C_{20}$ arylalkenyl, $C_9 \sim C_{20}$ aralkylalkenyl, $C_1 \sim C_{20}$ alkylthio, $C_2 \sim C_{20}$ alkoxyalkylthio, $C_2 \sim C_{20}$ alkylthioalkylthio, $C_2 \sim C_{20}$ alkenylthio, $C_7 \sim C_{20}$ aralkylthio, $C_8 \sim C_{20}$ aralkyloxyalkylthio, $C_8 \sim C_{20}$ aralkylthioalkylthio, $C_6 \sim C_{20}$ arylthio, $C_7 \sim C_{20}$ aryloxyalkylthio, $C_7 \sim C_{20}$ arylthioalkylthio, hetroalicyclic and halogen.

Further, aryl which is included in these substituents can be substituted with $C_1 \sim C_6$ alkyl, $C_1 \sim C_6$ alkoxy, $C_1 \sim C_6$ alkylthio, $C_7 \sim C_{10}$ aralkyl, $C_7 \sim C_{10}$ aralkyloxy, hydroxyl or halogen.

The aralkyl or aryl represented by $R_2$ can be monosubstituted or polysubstituted.

Exemplary substituents include, $C_1 \sim C_{20}$ alkyl, $C_2 \sim C_{20}$ alkenyl, $C_7 \sim C_{20}$ aralkyl, $C_6 \sim C_{20}$ aryl, $C_1 \sim C_{20}$ alkoxy, $C_2 \sim C_{20}$ alkoxyalkyl, $C_2 \sim C_{20}$ alkoxyalkyloxy, $C_2 \sim C_{20}$ alkenyloxy, $C_3 \sim C_{20}$ alkenyloxyalkyl, $C_3 \sim C_{20}$ alkenyloxyalkyloxy, $C_7 \sim C_{20}$ aralkyloxy, $C_8 \sim C_{20}$ aralkyloxyalkyl, $C_8 \sim C_{20}$ aralkyloxyalkyloxy, $C_6 \sim C_{20}$ aryloxy, $C_7 \sim C_{20}$ aryloxyalkyl, $C_7 \sim C_{20}$ aryloxyalkyloxy, $C_2 \sim C_{20}$ alkylcarbonyl, $C_3 \sim C_{20}$ alkenylcarbonyl, $C_8 \sim C_{20}$ aralkylcarbonyl, $C_7 \sim C_{20}$ arylcarbonyl, $C_2 \sim C_{20}$ alkoxycarbonyl, $C_3 \sim C_{20}$ alkenyloxycarbonyl, $C_8 \sim C_{20}$ aralkyloxycarbonyl, $C_7 \sim C_{20}$ aryloxycarbonyl, $C_2 \sim C_{20}$ alkylcarbonyloxy, $C_3 \sim C_{20}$ alkenylcarbonyloxy, $C_8 \sim C_{20}$ aralkylcarbonyloxy, $C_7 \sim C_{20}$ arylcarbonyloxy, $C_{14} \sim C_{20}$ aralkyloxyaralkyl, $C_1 \sim C_{20}$ alkylthio, $C_7 \sim C_{20}$ aralkylthio, $C_6 \sim C_{20}$ arylthio, nitro, formyl, halogen, hydroxy and cyano.

Aryl which is present in these substituents can be further substituted with $C_1 \sim C_6$ alkyl, $C_1 \sim C_6$ alkoxy, $C_1 \sim C_6$ alkylthio, $C_7 \sim C_{10}$ aralkyl, $C_7 \sim C_{10}$ aralkyloxy, hydroxy or halogen.

Preferred $R_2$ is unsubstituted or substituted alkyl having from 1 to 24 total carbon atoms, unsubstituted or substituted alkenyl having from 2 to 24 total carbon atoms, unsubstituted or substituted aralkyl having from 7 to 24 total carbon atoms, or unsubstituted or substituted aryl having from 6 to 24 total carbon atoms.

Exemplary $R_2$ include methyl, ethyl, n-propyl, isopropyl, n-butyl, isobutyl, sec-butyl, tert-butyl, n-pentyl, isopentyl, n-hexyl, 1-methylpentyl, 4-methyl-2-pentyl, n-heptyl, 1-methylhexyl, n-octyl, 1-methylheptyl, 2-ethylhexyl, n-nonyl, 2,6-dimethyl-4-heptyl, 3,5,5-trimethylhexyl, n-decyl, 1-ethyloctyl, n-undecyl, 1-methyldecyl, n-dodecyl, n-tridecyl, n-tetradecyl, n-pentadecyl, n-hexadecyl, n-heptadecyl, n-octadecyl, cyclopentyl, cyclohexyl, 4-methylcyclohexyl, 3-methylcyclohexyl, 2-methylcyclohexyl, 2,5-dimethylcyclohexyl, 2,6-dimethylcyclohexyl, 3,4-dimethylcyclohexyl, 3,5-dimethylcyclohexyl, 3,3,5-trimethylcyclohexyl, 4-tert-butylcyclohexyl, 3-tert-butylcyclohexyl, 4-phenylcyclohexyl, 2-phenylcyclohexyl, cycloheptyl, cyclooctyl, clyclohexylmethyl, 2-cyclohexylethyl, bornyl, isobornyl, 2-norbornylmethyl, 1-adamantylmethyl, vinyl, allyl, 2-butenyl, 3-butenyl, 1-methyl-4-pentenyl, 2-pentenyl, 4-pentenyl, 1-methyl-2-butenyl, 2-hexenyl, 3-hexenyl, 4-hexenyl, 5-hexenyl, 2-heptenyl, 1-vinylhexyl, 3-nonenyl, 6-nonenyl, 9-decenyl, 10-undecenyl, 1-cyclohexenyl, 2-methoxyethyl, 2-ethoxyethyl, 2-isopropoxyethyl, 2-n-butoxyethyl, 2-n-pentyloxyethyl, 2-heptyloxyethyl, 2-n-hexyloxyethyl, 2-n-octyloxyethyl, 2-n-decyloxyethyl, 2-n-dodecyloxyethyl, 2-cyclohexyloxyethyl, 3-n-methoxypropyl, 3-ethoxypropyl, 3-n-propoxypropyl, 3-n-butoxypropyl, 3-n-hexyloxypropyl, 3-n-octyloxypropyl, 3-cyclohexyloxypropyl, 4-ethoxybutyl, 5-methoxypentyl, 6-ethoxyhexyl, 2-methoxyethoxyethyl, 2-ethoxyethoxyethyl, 2-n-butoxyethoxyethyl, 3-ethoxyethoxypropyl, 2-allyloxyethyl, 2-(4'-pentenyl)oxyethyl, 3-allyloxypropyl, 4-allyloxybutyl, 2-benzyloxyethyl, 2-phenethyloxyethyl, 2-(4'-methylbenzyloxy)ethyl, 2-(4'-chlorobenzyloxy)ethyl, 3-benzyloxypropyl, 4-benzyloxybutyl, 2-benzyloxymethoxyethyl, 2-(4'-methylbenzyl)oxymethoxyethyl, phenoxymethyl, 2-phenoxyethyl, 2-(4'-chlorophenyloxy)ethyl, 2-(4'-methylphenyloxy)ethyl, 2-(4'-methoxyphenyloxy)ethyl, 3-phenoxypropyl, 4-phenoxybutyl, 6-(2'-chlorophenyloxy)hexyl, 2-phenoxyethoxyethyl, 2-(1'-naphthyloxy)ethyl, 2-(2'-naphthyloxy)ethyl, 3-(2'-naphthyloxy)propyl, cinnamyl, 2-methylthioethyl, 2-ethylthioethyl, 2-n-butylthioethyl, 2-n-hexylthioethyl, 2-n-octylthioethyl, 2-n-decylthioethyl, 3-methylthiopropyl, 3-ethylthiopropyl, 3-n-butylthiopropyl, 4-ethylthiobutyl, 4-n-propylthiobutyl, 4-n-butylthiobutyl, 5-ethylthiopentyl, 6-methylthiohexyl, 6-ethylthiohexyl, 6-n-butylthiohexyl, 8-methylthiooctyl, 2-methoxyethylthioethyl, 2-ethylthioethylthioethyl, 2-allylthioethyl, 2-benzylthioethyl, 3-(4'-methylbenzylthio)propyl, 4-benzylthiobutyl, 2-benzyloxyethylthioethyl, 3-benzylthiopropylthiopropyl, 2-phenylthioethyl, 2-(4'-methoxyphenylthio)ethyl, 2-phenoxyethylthioethyl, 3-(2'-chlorophenylthio)ethylthiopropyl, 2-tetrahydrofurfuryl, 2-chloroethyl, 3-chloropropyl, 2,2,2-trichloroethyl, 7-chloroheptyl, 8-chlorooctyl, 8-fluorooctyl, benzyl, α-methylbenzyl, α-ethylbenzyl, phenethyl, α-methylphenethyl, α,α-dimethylphenethyl, 4-methylphenethyl, 4-methylbenzyl, 3-methylbenzyl, 2-methylbenzyl, 4-isopropylbenzyl, 4-allylbenzyl, 4-benzylbenzyl, 4-phenethylbenzyl, 4-phenylbenzyl, 4-(4'-methylphenyl)benzyl, 4-methoxybenzyl, 4-n-butoxybenzyl, 3,4-dimethoxybenzyl, 4-methoxymethylbenzyl, 4-allyloxybenzyl, 4-vinyloxymethylbenzyl, 4-benzyloxybenzyl, 4-phenethyloxybenzyl, 4-phenoxybenzyl, 3-phenoxybenzyl, 4-hydroxybenzyl, 3-hydroxybenzyl, 2-hydroxybenzyl, 4-hydroxy-3-methoxybenzyl, 4-chlorobenzyl, 3-chlorobenzyl, 2-chlorobenzyl, 2-furfuryl, diphenylmethyl, phenyl, 1-naphthyl, 2-naphthyl, 3-furyl, 3-thienyl, 4-methylphenyl, 3-methylphenyl, 2-methylphenyl, 4-ethylphenyl, 3-ethylphenyl, 2-ethylphenyl, 4-n-propylphenyl, 4-isopropylphenyl, 4-n-butylphenyl, 4-sec-butylphenyl, 4-tert-butylphenyl, 4-n-pentylphenyl, 4-isopentylphenyl, 4-n-hexylphenyl, 4-n-heptylphenyl, 4-n-octylphenyl, 4-tert-octylphenyl, 4-n-decylphenyl, 4-n-dodecylphenyl, 4-cyclopenthylphenyl, 4-cyclohexylphenyl, 3-cyclohexylphenyl, 2-cyclohexylphenyl, 4-allylphenyl, 2-allylphenyl, 4-benzylphenyl, 2-benzylphenyl, 4-cumylphenyl, 4-(4'-methoxycumyl)phenyl, 4-(4'-benzyloxy)cumylphenyl, 4-(4'-chlorobenzyl)phenyl, 4-phenylphenyl, 3-phenylphenyl, 2-phenylphenyl, 4-(4'-methoxyphenyl)phenyl, 2-(2'-methoxyphenyl)phenyl, 4-(4'-chlorophenyl)phenyl, 4-methoxyphenyl, 3-methoxyphenyl, 2-methoxyphenyl, 4-ethoxyphenyl, 2-ethoxyphenyl, 3-n-propoxyphenyl, 4-isopropoxyphenyl, 4-n-butoxyphenyl, 4-isobutoxyphenyl, 4-n-pentyloxyphenyl, 4-isopentyloxyphenyl, 4-n-hexyloxyphenyl, 4-n-octyloxyphenyl, 4-n-decyloxyphenyl, 4-n-dodecyloxyphenyl, 4-cyclohexyloxyphenyl, 1-(4-ethylnaphthyl), 2-(6-butylnaphthyl), 1-(2-methoxynaphthyl), 1-(4-methoxynaphthyl), 1-(4-n-butoxynaphthyl), 1-(5-ethoxynaphthyl), 2-(6-ethoxynaphthyl), 2-(6-n-hexyloxynaphthyl), 2-(7-methoxynaphthyl), 2-(7-n-butoxynaphthyl), 4-methoxymethylphenyl, 4-ethoxymethylphenyl, 4-n-butoxymethylphenyl, 3-methoxymethylphenyl, 4(2'-methoxyethyl)phenyl, 4-(2'-ethoxyethyloxy)phenyl, 4-(2'-n-butoxyethyloxy)phenyl, 4-(3'-ethoxypropyloxy)phenyl, 4-vinyloxyphenyl, 4-allyloxyphenyl, 3-allyloxyphenyl, 4-(4'-pentenyloxyphenyl)phenyl, 1-(4-allyloxynaphthyl), 4-allyloxymethylphenyl, 4-(2'-allyloxyethyloxy)phenyl, 4-benzyloxyphenyl, 2-benzyloxyphenyl, 4-phenetyloxyphenyl, 4-(4'-chlorobenzyloxy)phenyl, 4-(4'-methylbenzyloxy)phenyl, 4-(4'-methoxybenzyloxy)phenyl, 4-(3'-ethoxybenzyloxy)phenyl, 1-(4-benzyloxynaphthyl), 2-(6-benzyloxynaphthyl), 2-(7-benzyloxynaphthyl), 4-(benzyloxymethyl)phenyl, 4-(2'-benzyloxyethyloxy)phenyl, 4-phenoxyphenyl, 3-phenoxyphenyl, 2-phenoxyphenyl, 4-(4'-methylphenoxy)phenyl, 4-(4'-methoxyphenoxy)phenyl, 4-(4'-chlorophenoxy)phenyl, 1-(4-phenoxynaphthyl), 4-phenoxymethylphenyl, 4-(2'-phenoxyethyloxy)phenyl, 4-[2'-(4'-methylphenyl)oxyethyloxy]phenyl, 4-[2'-(4'-methoxyphenyl)oxyethyloxy]phenyl, 4-[2'-(4'-chlorophenyl)oxyethyloxy]phenyl, 4-acetylphenyl, 3-acetylphenyl, 2-acetylphenyl, 4-ethylcarbonylphenyl, 4-n-butylcarbonylphenyl, 4-n-hexylcarbonylphenyl, 4-n-octylcarbonylphenyl, 4-cyclohexylcarbonylphenyl, 1-(4-acetylnaphthyl), 4-allylcarbonylphenyl, 4-benzylcarbonylphenyl, 4-(4'-methylbenzyl)carbonylphenyl, 4-phenylcarbonylphenyl, 4-(4'-methylphenyl)carbonylphenyl, 4-(4'-chlorophenyl)carbonylphenyl, 1-(4-phenylcarbonylnaphthyl), 4-methoxycarbonylphenyl, 2-methoxycarbonylphenyl, 4-ethoxycarbonylphenyl, 3-ethoxycarbonylphenyl, 4-n-propoxycarbonylphenyl, 4-n-butoxycarbonylphenyl, 4-n-hexyloxycarbonylphenyl, 4-n-decyloxycarbonylphenyl, 4-cyclohexyloxycarbonylphenyl, 1-(4-ethoxycarbonylnaphthyl), 2-(6-methoxycarbonylnaphthyl), 2-(6-n-butoxycarbonylnaphthyl), 4-allyloxycarbonylphenyl, 4-benzyloxycarbonylphenyl, 4-(4'-chlorobenzyl)oxycarbonylphenyl, 4-phenetyloxycarbonylphenyl, 2-(6-benzyloxycarbonylnaphthyl), 4-phenyloxycarbonylphenyl, 4-(4'-ethylphenyl)oxycarbonylphenyl, 4-(4'-chlorophenyl)oxycarbonylphenyl, 4-(4'-ethoxyphenyl)oxycarbonylphenyl, 2-(6-phenyloxycarbonylnaphthyl), 4-acetyloxyphenyl, 3-acetyloxyphenyl, 4-ethylcarbonyloxyphenyl, 2-ethylcarbonyloxyphenyl, 4-n-propylcarbonyloxyphenyl, 4-n-pentylcarbonyloxyphenyl, 4-n-octylcarbonyloxyphenyl, 4-cyclohexylcarbonyloxyphenyl, 1-(4-acetyloxynaphthyl), 1-(5-acetyloxynaphthyl), 2-(6-ethylcarbonyloxynaphthyl), 4-allylcarbonyloxyphenyl, 4-benzylcarbonyloxyphenyl, 4-phenethylcarbonyloxyphenyl, 2-(6-benzylcarbonyloxynaphthyl), 4-phenylcarbonyloxyphenyl, 4-(4'-methylphenyl)carbonyloxyphenyl, 4-(2'-methylphenyl)carbonyloxyphenyl, 4-(4'-chlorophenyl)carbonyloxyphenyl, 4-(2'-chlorophenyl)carbonyloxyphenyl, 1-(4-phenylcarbonyloxynaphthyl), 2-(6-phenylcarbonyloxynaphthyl), 4-methylthiophenyl, 2-methylthiophenyl, 4-ethylthiophenyl, 3-ethylthiophenyl, 4-n-propylthiophenyl, 4-n-butylthiophenyl, 4-n-hexylthiophenyl, 4-n-octylthiophenyl, 4-cyclohexylthiophenyl, 4-benzylthiophenyl, 3-benzylthiophenyl, 4-(4'-chlorobenzylthio)phenyl, 4-phenylthiophenyl, 3-phenylthiophenyl, 4-(4'-methylphenylthio)phenyl, 4-(4'-methoxyphenylthio)phenyl, 4-(4'-chlorophenylthio)phenyl, 1-(4-methylthionaphthyl), 2-(6-ethylthionaphthyl), 2-(6-phenylthionaphthyl), 4-fluorophenyl, 3-fluorophenyl, 2-fluorophenyl, 4-chlorophenyl, 3-chlorophenyl, 2-chlorophenyl, 4-bromophenyl, 1-(4-chloronaphthyl), 2-(4-chloronaphthyl), 2-(6-bromonaphthyl), 4-nitrophenyl, 3-nitrophenyl, 4-formylphenyl, 3-formylphenyl, 2-formylphenyl, 1-(4-formylnaphthyl), 2-(1-formylnaphthyl), 4-hydroxyphenyl, 3-hydroxyphenyl, 2-hydroxyphenyl, 1-(4-hydroxynaphthyl), 2-(6-hydroxynaphthyl), 4-cyanophenyl, 2-cyanophenyl, 2-(6-cyanonaphthyl), 2-chloro-4-nitrophenyl, 4-chloro-2-nitrophenyl, 6-chloro-3-methylphenyl, 2-chloro-6-methylphenyl, 4-chloro-2-methylphenyl, 4-chloro-3-methylphenyl, 2,4-dimethylphenyl, 2,5,-dimethylphenyl, 3,4-dimethylphenyl, 3,5-dimethylphenyl, 2,6-dimethylphenyl, 2,3,5-trimethylphenyl, 2,3,6-trimethylphenyl, 2,4,6-trimethylphenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,6-trichlorophenyl, 2-methoxy-4-methylphenyl, 2,6-dimethoxyphenyl, 3,5-dimethoxyphenyl, 3,5-diethoxyphenyl, 3,5-di-n-butoxyphenyl, 3,4,5-trimethoxyphenyl and 1-(2,4-dichloronaphthyl).

The compound represented by the formula (1) in the invention has a carbamate group on a salicylic acid skeleton. The carbamate group locates on the position 3, 4, 5 or 6, preferably on the position 3, 4 or 5, most preferably on the position 4 or 5 in the salicylic acid skeleton. That is, most preferred salicylic acid derivative is represented by the formula (1-a):

wherein $X_1$, $X_2$, $Y_1$, $Y_2$, $R_1$ and $R_2$ are the same as above, or by the formula (1-b):

wherein $X_1$, $X_2$, $Y_1$, $Y_2$, $R_1$ and $R_2$ are the same as above.

Exemplary salicylic acid derivative represented by the formula (1) and the metal salt of the derivative which can be used for the invention will be enumerated below. However, it is to be understood that the invention is not limited by the following compounds.

| No. | Compound |
|---|---|
| 1) | 3-(isopropyloxycarbonylamino)salicylic acid |
| 2) | 3-(isopentyloxycarbonylamino)salicylic acid |
| 3) | 3-(n-hexyloxycarbonylamino)salicylic acid |
| 4) | 3-(n-octyloxycarbonylamino)salicylic acid |
| 5) | 3-(n-decyloxycarbonylamino)salicylic acid |
| 6) | 3-[(4'-methylcyclohexyl)oxycarbonylamino]salicylic acid |
| 7) | 3-[(2'-cyclohexylethyl)oxycarbonylamino]salicylic acid |
| 8) | 3-(allyloxycarbonylamino)salicylic acid |
| 9) | 3-[(2'-hexenyl)oxycarbonylamino]salicylic acid |
| 10) | 3-[(2'-ethoxyethyl)oxycarbonylamino]salicylic acid |
| 11) | 3-[(3'-n-hexyloxypropyl)oxycarbonylamino]salicylic acid |
| 12) | 3-[(2'-benzyloxyethyl)oxycarbonylamino]salicylic acid |
| 13) | 3-(phenoxymethyloxycarbonylamino)salicylic acid |
| 14) | 3-[(2'-phenoxyethyl)oxycarbonylamino]salicylic acid |
| 15) | 3-[(2'-(4-chlorophenyl)oxyethyloxycarbonylamino]salicylic acid |
| 16) | 3-[2'-(4-methoxyphenyl)oxyethyloxycarbonylamino)salicylic acid |
| 17) | 3-[(2'-phenoxyethoxyethyl)oxycarbonylamino]salicylic acid |
| 18) | 3-(cinnamyloxycarbonylamino)salicylic acid |
| 19) | 3-[(2'-n-butylthioethyl)oxycarbonylamino]salicylic acid |
| 20) | 3-[(2'-methoxyethylthioethyl)oxycarbonylamino]salicylic acid |
| 21) | 3-[(2'-allylthioethyl)oxycarbonylamino]salicylic acid |
| 22) | 3-[(2'-benzylthioethyl)oxycarbonylamino]salicylic acid |
| 23) | 3-[(2'-phenylthioethyl)oxycarbonylamino]salicylic acid |
| 24) | 3-[(7'-chloroheptyl)oxycarbonylamino]salicylic acid |
| 25) | 3-(benzyloxycarbonylamino)salicylic acid |
| 26) | 3-[(4'-methylbenzyl)oxycarbonylamino]salicylic acid |
| 27) | 3-[(4'-chlorobenzyl)oxycarbonylamino]salicylic acid |
| 28) | 3-[(3'-phenoxybenzyl)oxycarbonylamino]salicylic acid |
| 29) | 3-(phenyloxycarbonylamino)salicylic acid |
| 30) | 3-[8 (2'-naphthyl oxycarbonylamino]salicylic acid |
| 31) | 3-[(3'-furyl)oxycarbonylamino]salicylic acid |
| 32) | 3-[(3'-phenylphenyl)oxycarbonylamino]salicylic acid |
| 33) | 3-[(4'-methylphenyl)oxycarbonylamino]salicylic acid |
| 34) | 3-[(4'-n-butylphenyl)oxycarbonylamino]salicylic acid |
| 35) | 3-[(4'-tert-butylphenyl)oxycarbonylamino]salicylic acid |
| 36) | 3-[(4'-cyclohexylphenyl)oxycarbonylamino]salicylic acid |
| 37) | 3-[(3'-methoxyphenyl)oxycarbonylamino]salicylic acid |
| 38) | 3-[(4'-n-butoxyphenyl)oxycarbonylamino]salicylic acid |
| 39) | 3-[(4'-n-octyloxyphenyl)oxycarbonylamino]salicylic acid |
| 40) | 3-[(4'-phenoxyphenyl)oxycarbonylamino]salicylic acid |
| 41) | 3-[(2'-acetylphenyl)oxycarbonylamino]salicylic acid |
| 42) | 3-[(4'-allylcarbonylphenyl)oxycarbonylamino]salicylic acid |

| No. | Compound |
|---|---|
| 43) | 3-[(4'-phenylcarbonylphenyl)oxycarbonylamino]salicylic acid |
| 44) | 3-[(4'-n-butoxycarbonylphenyl)oxycarbonylamino]salicylic acid |
| 45) | 3-[(4'-benzyloxyphenyl)oxycarbonylamino]salicylic acid |
| 46) | 3-[(4'-acetyloxyphenyl)oxycarbonylamino]salicylic acid |
| 47) | 3-[(4'-ethylthiophenyl)oxycarbonylamino]salicylic acid |
| 48) | 3-[(4'-fluorophenyl)oxycarbonylamino]salicylic acid |
| 49) | 3-[(4'-chlorophenyl)oxycarbonylamino]salicylic acid |
| 50) | 3-[(4'-nitrophenyl)oxycarbonylamino]salicylic acid |
| 51) | 3-[(4'-formylphenyl)oxycarbonylamino]salicylic acid |
| 52) | 3-[(4'-hydroxyphenyl)oxycarbonylamino]salicylic acid |
| 53) | 3-[(4'-cyanophenyl)oxycarbonylamino]salicylic acid |
| 54) | 3-[(2',4'-dimethylphenyl)oxycarbonylamino]salicylic acid |
| 55) | 3-[(3',5'-dichlorophenyl)oxycarbonylamino]salicylic acid |
| 56) | 5-methyl-3-(n-hexyloxycarbonylamino)salicylic acid |
| 57) | 5-cyclohexyl-3-(phenyloxycarbonylamino)salicylic acid |
| 58) | 5-cumyl-3-(n-hexyloxycarbonylamino)salicylic acid |
| 59) | 3-(n-octylthiolcarbonylamino)salicylic acid |
| 60) | 3-(4'-chlorobenzyl)thiolcarbonylamino]salicylic acid |
| 61) | 3-[(3'-methylphenyl)thiolcarbonylamino]salicylic acid |
| 62) | 3-(n-butylthiolthiocarbonylamino)salicylic acid |
| 63) | 3-(phenylthiolthiocarbonylamino)salicylic acid |
| 64) | 3-[(4'-ethoxyphenyl)thiolthiocarbonylamino]salicylic acid |
| 65) | 3-(N-phenyl-N-phenyloxycarbonylamino)salicylic acid |
| 66) | 4-(methyloxycarbonylamino)salicylic acid |
| 67) | 4-(ethyloxycarbonylamino)salicylic acid |
| 68) | 4-(n-propyloxycarbonylamino)salicylic acid |
| 69) | 4-(isopropyloxycarbonylamino)salicylic acid |
| 70) | 4-(n-butyloxycarbonylamino)salicylic acid |
| 71) | 4-(isobutyloxycarbonylamino)salicylic acid |
| 72) | 4-(sec-butyloxycarbonylamino)salicylic acid |
| 73) | 4-(n-pentyloxycarbonylamino)salicylic acid |
| 74) | 4-(isopentyloxycarbonylamino)salicylic acid |
| 75) | 4-(n-hexyloxycarbonylamino)salicylic acid |
| 76) | 4-(n-heptyloxycarbonylamino)salicylic acid |
| 77) | 4-(n-octyloxycarbonylamino)salicylic acid |
| 78) | 4-[(2'-ethylhexyl)oxycarbonylamino]salicylic acid |
| 79) | 4-(n-nonyloxycarbonylamino)salicylic acid |
| 80) | 4-(n-decyloxycarbonylamino)salicylic acid |
| 81) | 4-(n-undecyloxycarbonylamino)salicylic acid |
| 82) | 4-(n-dodecyloxycarbonylamino)salicylic acid |
| 83) | 4-(n-tridecyloxycarbonylamino)salicylic acid |
| 84) | 4-(n-tetradecyloxycarbonylamino)salicylic acid |
| 85) | 4-(n-pentadecyloxycarbonylamino)salicylic acid |
| 86) | 4-(n-hexadecyloxycarbonylamino)salicylic acid |
| 87) | 4-(n-heptadecyloxycarbonylamino)salicylic acid |
| 88) | 4-(n-octadecyloxycarbonylamino)salicylic acid |
| 89) | 4-(cyclopentyloxycarbonylamino)salicylic acid |
| 90) | 4-(cyclohexyloxycarbonylamino)salicylic acid |
| 91) | 4-[(4'-tert-butylcyclohexyl)oxycarbonylamino]salicylic acid |
| 92) | 4-(cycloheptyloxycarbonylamino)salicylic acid |
| 93) | 4-(cyclooctyloxycarbonylamino)salicylic acid |
| 94) | 4-(cyclohexylmethyloxycarbonylamino)salicylic acid |
| 95) | 4-[(2'-tetrahydrofurfuryl)oxycarbonylamino]salicylic acid |
| 96) | 4-[(2'-methoxyethyl)oxycarbonylamino]salicylic acid |
| 97) | 4-[(2'-n-hexyloxyethyl)oxycarbonylamino]salicylic acid |
| 98) | 4-[(2'-n-octyloxyethyl)oxycarbonylamino]salicylic acid |
| 99) | 4-[(3'-ethoxypropyl)oxycarbonylamino]salicylic acid |
| 100) | 4-[(3'-n-butoxypropyl)oxycarbonylamino]salicylic acid |
| 101) | 4-[(3'-n-octyloxypropyl)oxycarbonylamino]salicylic acid |
| 102) | 4-[(2'-n-butoxyethoxyethyl)oxycarbonylamino]salicylic acid |
| 103) | 4-[(2'-benzyloxyethyl)oxycarbonylamino]salicylic acid |
| 104) | 4-[(phenoxymethyl)oxycarbonylamino]salicylic acid |
| 105) | 4-[(2'-phenoxyethyl)oxycarbonylamino]salicylic acid |
| 106) | 4-[2'-(4-chlorophenyl)oxyethyloxycarbonylamino]salicylic acid |
| 107) | 4-[2'-(4-methoxyphenyl)oxyethyloxycarbonylamino]salicylic acid |
| 108) | 4-[(2'-phenoxyethoxyethyl)oxycarbonylamino]salicylic acid |
| 109) | 4-[(3'-n-butylthiopropyl)oxycarbonylamino]salicylic acid |
| 110) | 4-[(6'-ethylthiohexyl)oxycarbonylamino]salicylic acid |
| 111) | 4-[(2'-benzylthioethyl)oxycarbonylamino]salicylic acid |
| 112) | 4-[(2'-phenylthioethyl)oxycarbonylamino]salicylic acid |
| 113) | 4-[(2'-chloroethyl)oxycarbonylamino]salicylic acid |
| 114) | 4-[(9'-decenyl)oxycarbonylamino]salicylic acid |
| 115) | 4-(benzyloxycarbonylamino)salicylic acid |
| 116) | 4-[(4'-methylbenzyl)oxycarbonylamino]salicylic acid |
| 117) | 4-[(4'-chlorobenzyl)oxycarbonylamino]salicylic acid |
| 118) | 4-[(2'-phenylethyl)oxycarbonylamino]salicylic acid |
| 119) | 4-(phenyloxycarbonylamino)salicylic acid |
| 120) | 4-[(1'-naphthyl)oxycarbonylamino]salicylic acid |
| 121) | 4-[(2'-naphthyl)oxycarbonylamino]salicylic acid |
| 122) | 4-[(2'-furyl)oxycarbonylamino]9 salicylic acid |
| 123) | 4-[(4'-phenylphenyl)oxycarbonylamino]salicylic acid |
| 124) | 4-[(4'-methylphenyl)oxycarbonylamino]salicylic acid |
| 125) | 4-[(3'-methylphenyl)oxycarbonylamino]salicylic acid |
| 126) | 4-[(2'-methylphenyl)oxycarbonylamino]salicylic acid |
| 127) | 4-[(4'-ethylphenyl)oxycarbonylamino]salicylic acid |
| 128) | 4-[(4'-tert-butylphenyl)oxycarbonylamino]salicylic acid |
| 129) | 4-[(4'-cyclohexylphenyl)oxycarbonylamino]salicylic acid |
| 130) | 4-[(2'-cyclohexylphenyl)oxycarbonylamino]salicylic acid |
| 131) | 4-[(4'-cumylphenyl)oxycarbonylamino]salicylic acid |
| 132) | 4-[(4'-methoxyphenyl)oxycarbonylamino]salicylic acid |
| 133) | 4-[(3'-methoxyphenyl)oxycarbonylamino]salicylic acid |
| 134) | 4-[(2'-ethoxyphenyl)oxycarbonylamino]salicylic acid |
| 135) | 4-[(4'-n-butoxyphenyl)oxycarbonylamino]salicylic acid |
| 136) | 4-[(4'-n-hexyloxyphenyl)oxycarbonylamino]salicylic acid |
| 137) | 4-[(4'-benzyloxyphenyl)oxycarbonylamino]salicylic acid |
| 138) | 4-[4'-(4-benzyloxycumyl)phenyloxycarbonylamino]salicylic acid |
| 139) | 4-[(4'-phenoxyphenyl)oxycarbonylamino]salicylic acid |
| 140) | 4-[2'-(6-benzyloxy)naphthyloxycarbonylamino]salicylic acid |
| 141) | 4-[(4'-phenylcarbonylphenyl)oxycarbonylamino]salicylic acid |
| 142) | 4-[(4'-acetylphenyl)oxycarbonylamino]salicylic acid |
| 143) | 4-[(4'-ethoxycarbonylphenyl)oxycarbonylamino]salicylic acid |
| 144) | 4-[(4'-cyclohexyloxycarbonylphenyl)oxycarbonylamino]-salicylic acid |
| 145) | 4-[(4'-n-propylcarbonyloxyphenyl)oxycarbonylamino]-salicylic acid |
| 146) | 4-[(4'-n-methylthiophenyl)oxycarbonylamino]salicylic acid |
| 147) | 4-[(4'-benzylthiophenyl)oxycarbonylamino]salicylic acid |
| 148) | 4-[(4'-fluorophenyl)oxycarbonylamino]salicylic acid |
| 149) | 4-[(2'-fluorophenyl)oxycarbonylamino]salicylic acid |
| 150) | 4-[(4'-chlorophenyl oxycarbonylamino]salicylic acid |
| 151) | 4-(3'-chlorophenyl)oxycarbonylamino]salicylic acid |
| 152) | 4-[(4'-bromophenyl)oxycarbonylamino]salicylic acid |
| 153) | 4-[(4'-nitrophenyl)oxycarbonylamino]salicylic acid |
| 154) | 4-[(4'-formylphenyl)oxycarbonylamino]salicylic acid |
| 155) | 4-[(4'-cyanophenyl)oxycarbonylamino]salicylic acid |
| 156) | 4-[(2',4'-dimethylphenyl)oxycarbonylamino]salicylic acid |
| 157) | 4-[(3',5'-dimethylphenyl)oxycarbonylamino]salicylic acid |
| 158) | 4-[(2',4'-dichlorophenyl)oxycarbonylamino]salicylic acid |
| 159) | 4-[(3',5'-dimethoxyphenyl)oxycarbonylamino]salicylic acid |
| 160) | 4-[(3'-nitro-4'-chlorophenyl)oxycarbonylamino]salicylic acid |
| 161) | 4-[(4'-chloro-2'-methylphenyl)oxycarbonylamino]salicylic acid |
| 162) | 4-(n-octylthiolcarbonylamino)salicylic acid |
| 163) | 4-(phenylthiolcarbonylamino)salicylic acid |
| 164) | 4-[(4'-ethoxyphenylthiol)carbonylamino]salicylic acid |
| 165) | 4-(n-hexylthiolthiocarbonylamino)salicylic acid |
| 166) | 4-[(4'-methylphenylthiol)thiocarbonylamino]salicylic acid |
| 167) | 4-(n-decyloxythiocarbonylamino)salicylic acid |
| 168) | 4-(N-n-butyl-N-heptyloxycarbonylamino)salicylic acid |
| 169) | 3-ethyl-4-(phenyloxycarbonylamino)salicylic acid |
| 170) | 3-chloro-4-(n-butyloxycarbonylamino)salicylic acid |
| 171) | 5-(methyloxycarbonylamino)salicylic acid |
| 172) | 5-(ethyloxycarbonylamino)salicylic acid |
| 173) | 5-(n-propyloxycarbonylamino)salicylic acid |
| 174) | 5-(n-butyloxycarbonylamino)salicylic acid |
| 175) | 5-(isobutyloxycarbonylamino)salicylic acid |
| 176) | 5-(n-pentyloxycarbonylamino)salicylic acid |
| 177) | 5-(isopentyloxycarbonylamino)salicylic acid |
| 178) | 5-(n-hexyloxycarbonylamino)salicylic acid |
| 179) | 5-(n-heptyloxycarbonylamino)salicylic acid |
| 180) | 5-(n-octyloxycarbonylamino)salicylic acid |
| 181) | 5-[(2'-ethylhexyl)oxycarbonylamino]salicylic acid |
| 182) | 5-(n-nonyloxycarbonylamino)salicylic acid |
| 183) | 5-(n-decyloxycarbonylamino)salicylic acid |
| 184) | 5-(n-undecyloxycarbonylamino)salicylic acid |
| 185) | 5-(n-dodecyloxycarbonylamino)salicylic acid |
| 186) | 5-(n-tetradecyloxycarbonylamino)salicylic acid |
| 187) | 5-(n-hexadecyloxycarbonylamino)salicylic acid |
| 188) | 5-(cyclohexyloxycarbonylamino)salicylic acid |
| 189) | 5-[(4'-methylcyclohexyl)oxycarbonylamino]salicylic acid |
| 190) | 5-[(4'-tert-butylcyclohexyl)oxycarbonylamino]salicylic acid |
| 191) | 5-[(2'-cyclohexylethyl)oxycarbonylamino]salicylic acid |
| 192) | 5-(cyclooctyloxycarbonylamino)salicylic acid |
| 193) | 5-[(2'-tetrahydrofurfuryl)oxycarbonylamino]salicylic acid |
| 194) | 5-[(2'-methoxyethyl)oxycarbonylamino]salicylic acid |

-continued

| No. | Compound |
|---|---|
| 195) | 5-[(2'-n-hexyloxyethyl)oxycarbonylamino]salicylic acid |
| 196) | 5-[(3'-ethoxypropyl)oxycarbonylamino]salicylic acid |
| 197) | 5-[(3'-isopropoxypropyl)oxycarbonylamino]salicylic acid |
| 198) | 5-[(2'-methoxyethoxyethyl)oxycarbonylamino]salicylic acid |
| 199) | 5-(phenoxymethyloxycarbonylamino)salicylic acid |
| 200) | 5-(2'-phenoxyethyloxycarbonylamino)salicylic acid |
| 201) | 5-[2'-(4-chlorophenyl)oxyethyloxycarbonylamino]salicylic acid |
| 202) | 5-[2'-(4-methoxyphenyl)oxyethyloxycarbonylamino]salicylic acid |
| 203) | 5-[(2'-phenoxyethoxyethyl)oxycarbonylamino]salicylic acid |
| 204) | 5-[(2'-n-hexylthioethyl)oxycarbonylamino]salicylic acid |
| 205) | 5-[(2'-phenylthioethyl)oxycarbonylamino]salicylic acid |
| 206) | 5-(2'-chloroethyloxycarbonylamino)salicylic acid |
| 207) | 5-(5'-hexenyloxycarbonylamino)salicylic acid |
| 208) | 5-(benzyloxycarbonylamino)salicylic acid |
| 209) | 5-[(4'-methylbenzyl)oxycarbonylamino]salicylic acid |
| 210) | 5-[(4'-chlorobenzyl)oxycarbonylamino]salicylic acid |
| 211) | 5-[(2'-phenylethyl)oxycarbonylamino]salicylic acid |
| 212) | 5-(phenyloxycarbonylamino)salicylic acid |
| 213) | 5-[(2'-naphthyl)oxycarbonylamino]salicylic acid |
| 214) | 5-[(4'-phenylphenyl)oxycarbonylamino]salicylic acid |
| 215) | 5-[(3'40 -methylphenyl)oxycarbonylamino]salicylic acid |
| 216) | 5-[(4'-ethylphenyl)oxycarbonylamino]salicylic acid |
| 217) | 5-[(4'-cyclohexylphenyl)oxycarbonylamino]salicylic acid |
| 218) | 5-[(4'-cumylphenyl)oxycarbonylamino]salicylic acid |
| 219) | 5-[(4'-methoxyphenyl)oxycarbonylamino]salicylic acid |
| 220) | 5-[(3'-ethoxyphenyl)oxycarbonylamino]salicylic acid |
| 221) | 5-[(4'-n-butoxyphenyl)oxycarbonylamino]salicylic acid |
| 222) | 5-[(4'-phenoxyphenyl)oxycarbonylamino]salicylic acid |
| 223) | 5-[(4'-acetylphenyl)oxycarbonylamino]salicylic acid |
| 224) | 5-[(4'-methoxycarbonylphenyl)oxycarbonylamino]salicylic acid |
| 225) | 5-[(4'-ethylcarbonyloxyphenyl)oxycarbonylamino]salicylic acid |
| 226) | 5-[(4'-ethylthiophenyl)oxycarbonylamino]salicylic acid |
| 227) | 5-[(4'-phenylthiophenyl)oxycarbonylamino]salicylic acid |
| 228) | 5-[(4'-fluorophenyl)oxycarbonylamino]salicylic acid |
| 229) | 5-[(3'-fluorophenyl)oxycarbonylaminosalicylic acid |
| 230) | 5-[(4'-chlorophenyl)oxycarbonylamino]salicylic acid |
| 231) | 5-[(3'-chlorophenyl)oxycarbonylamino]salicylic acid |
| 232) | 5-[(2'-chlorophenyl)oxycarbonylamino]salicylic acid |
| 233) | 5-[(2'-formylphenyl)oxycarbonylamino]salicylic acid |
| 234) | 5-[(2'-cyanophenyl)oxycarbonylamino]salicylic acid |
| 235) | 5-[(2',4'-dimethylphenyl)oxycarbonylamino]salicylic acid |
| 236) | 5-[(3',5'-dimethylphenyl)oxycarbonylamino]salicylic acid |
| 237) | 5-[(3'-nitro-4'-chlorophenyl)oxycarbonylamino]salicylic acid |
| 238) | 5-(n-butylthiolcarbonylamino)salicylic acid |
| 239) | 5-(phenylthiolcarbonylamino)salicylic acid |
| 240) | 5-[(2'-naphthylthiol)carbonylamino]salicylic acid |
| 241) | 5-[(4'-methylphenylthiol)carbonylamino]salicylic acid |
| 242) | 5-(n-heptylthiolthiocarbonylamino)salicylic acid |
| 243) | 5-(n-dodecylthiolthiocarbonylamino)salicylic acid |
| 244) | 5-(n-pentyloxythiocarbonylamino)salicylic acid |
| 245) | 5-[(4'-chlorophenyl)oxythiocarbonylamino]salicylic acid |
| 246) | 5-(N-methyl-N-phenyloxycarbonylamino)salicylic acid |
| 247) | 3-methyl-5-(methyloxycarbonylamino)salicylic acid |
| 248) | 3-ethoxy 5-(n-butyloxycarbonylamino)salicylic acid |
| 249) | 3-α-methylbenzyl-5-(ethyloxycarbonylamino)salicylic acid |
| 250) | 3-phenyl-5-(n-hexyloxycarbonylamino)salicylic acid |
| 251) | 6-(n-propyloxycarbonylamino)salicylic acid |
| 252) | 6-(isopentyloxycarbonylamino)salicylic acid |
| 253) | 6-(n-heptyloxycarbonylamino)salicylic acid |
| 254) | 6-[(1'-methylheptyl)oxycarbonylamino]salicylic acid |
| 255) | 6-(n-dodecyloxycarbonylamino)salicylic acid |
| 256) | 6-[(2',5'-dimethylcyclohexyl)oxycarbonylamino]salicylic acid |
| 257) | 6-[(2'-cyclohexylmethyl)oxycarbonylamino]salicylic acid |
| 258) | 6-[(3'-butenyl)oxycarbonylamino]salicylic acid |
| 259) | 6-[(10'-undecenyl)oxycarbonylamino]salicylic acid |
| 260) | 6-[(2'-isopropoxyethyl)oxycarbonylamino]salicylic acid |
| 261) | 6-[(3'-cyclohexyloxypropyl)oxycarbonylamino]salicylic acid |
| 262) | 6-[(2'-phenethyloxyethyl)oxycarbonylamino]salicylic acid |
| 263) | 6-[(2'-phenoxyethyl)oxycarbonylamino]salicylic acid |
| 264) | 6-[(2'-(4-chlorophenoxy)ethyloxycarbonylamino]salicylic acid |
| 265) | 6-[(3'-n-buthylthiopropyl)oxycarbonylamino]salicylic acid |
| 266) | 6-[(3'-(4-methylbenzylthio)propyloxycarbonylamino]-salicylic acid |
| 267) | 6-[(2'-phenylthioethyl)oxycarbonylamino]salicylic acid |
| 268) | 6-[(2'-tetrahydrofurfuryl)oxycarbonylamino]salicylic acid |
| 269) | 6-[(2'-chloroethyl)oxycarbonylamino]salicylic acid |
| 270) | 6-(benzyloxycarbonylamino)salicylic acid |
| 271) | 6-[(4'-chlorobenzyl)oxycarbonylamino]salicylic acid |
| 272) | 6-(phenyloxycarbonylamino)salicylic acid |
| 273) | 6-[(1'-naphthyl)oxycarbonylamino]salicylic acid |
| 274) | 6-[(4'-phenylphenyl)oxycarbonylamino]salicylic acid |
| 275) | 6-[(2'-ethylphenyl)oxycarbonylamino]9 salicylic acid |
| 276) | 6-[(4'-tert-butylphenyl)oxycarbonylamino]salicylic acid |
| 277) | 6-[(3'-methoxyphenyl)oxycarbonylamino]salicylic acid |
| 278) | 6-[(4'-n-hexyloxyphenyl)oxycarbonylamino]salicylic acid |
| 279) | 6-[(3'-phenoxyphenyl)oxycarbonylamino]salicylic acid |
| 280) | 6-[(4'-ethylcarbonylphenyl)oxycarbonylamino]salicylic acid |
| 281) | 6-[(4'-benzylcarbonylphenyl)oxycarbonylamino]salicylic acid |
| 282) | 6-[(4'-methoxycarbonylphenyl)oxycarbonylamino]salicylic acid |
| 283) | 6-[(4'-methylthiophenyl)oxycarbonylamino]salicylic acid |
| 284) | 6-[(3'-fluorophenyl)oxycarbonylamino]salicylic acid |
| 285) | 6-[(2'-chlorophenyl)oxycarbonylamino]salicylic acid |
| 286) | 6-[(3'-nitrophenyl)oxycarbonylamino]salicylic acid |
| 287) | 6-[(2'-formylphenyl)oxycarbonylamino]salicylic acid |
| 288) | 6-[(3'-hydroxyphenyl)oxycarbonylamino]salicylic acid |
| 289) | 6-[(4'-cyanophenyl)oxycarbonylamino]salicylic acid |
| 290) | 6-[(3',4'-dimethylphenyl)oxycarbonylamino]salicylic acid |
| 291) | 6-[(2',4'-dichlorophenyl)oxycarbonylamino]salicylic acid |
| 292) | 3-ethyl-6-(n-hexyloxycarbonylamino)salicylic acid |
| 293) | 3-tert-butyl-6-(phenyloxycarbonylamino)salicylic acid |
| 294) | 6-(N-ethyl-N-phenyloxycarbonylamino)salicylic acid |
| 295) | 6-(n-octylthiolcarbonylamino)salicylic acid |
| 296) | 6-[(4'-methylbenzyl)thiolcarbonylamino]salicylic acid |
| 297) | 6-[(4'-methylphenyl)thiolcarbonylamino]salicylic acid |
| 298) | 6-(n-octylthiolthiocarbonylamino)salicylic acid |
| 299) | 6-(phenylthiolthiocarbonylamino)salicylic acid |
| 300) | 6-[(4'-methoxyphenyl)thiolthiocarbonylamino]salicylic acid |

The metal salt of salicylic acid derivative represented by the formula (1) which is used for the electron accepting compound in the heat-sensitive recording material of the invention includes salts of monovalent metals such as sodium, potassium and lithium and polyvalent metals having 2, 3 and 4 valence. In the case of using the metal salt singly as an electron accepting compound, the salt is preferably a metal salt which is difficultly soluble or insoluble in water and composed of a polyvalent metal of 2, 3 and 4 valence, more preferably a salt of the polyvalent metal having 2 or 3 valence.

Exemplary salts of the polyvalent metal are salts of zinc, cadmium, mercury, magnesium, calcium, barium, nickel, tin, lead, gallium, chromium, copper, molybdenum, wolfram, zirconium, strontium, manganese, cobalt, titanium, aluminum and iron, preferably salts of zinc, magnesium, calcium, barium, nickel, manganese, cobalt and aluminum, more preferably salts of zinc, magnesium, nickel and manganese, most preferably a zinc salt.

Any of the salicylic acid derivatives enumerated above can form salts of the metal having from 1 to 4 valence. The metal salt of the salicylic acid derivative can be used for the heat-sensitive recording material of the invention. The salicylic acid derivative represented by the formula (1) and the metal salt of the derivative can be used singly or as a mixture for the electron accepting compound in the heat-sensitive recording material of the invention. For example, a combination of one or more salicylic acid derivative and a metal salt of salicylic acid derivative can also be used.

The salicylic acid derivative represented by the formula (1) in the invention can be prepared by various processes.

The preparation process of the invention is particularly preferred.

In the process of the invention, the aminosalicylic acid derivative represented by the formula (2):

wherein $X_1$, $X_2$ and $R_1$ is the same as above, is reacted with a compound represented by the formula (3):

wherein $Y_1$, $Y_2$ and $R_2$ are the same as above and Z is a halogen atom, in the presence of an alcohol-based solvent to obtain the salicylic acid derivative represented by the formula (1).

The preparation process of the salicylic acid derivative of the invention is characterized by conducting the reaction in the presence of an alcohol-based solvent. It has not yet been known to prepare the compound of the formula (1) in the presence of such a solvent.

It has been already mentioned that some of the compounds represented by the formula (1) were prepared by reacting the compound of the formula (2) with the compound of the formula (3). As a solvent in carrying out the reaction, dry pyridine was used in German Patent 2749518 and water was used in Bull. de. Socie. Chim. France, 1189 (1955) and J. Pharm. Sci., 52, 927 (1963).

These known reaction solvents led to the low yield or formation of by-products and thus the salicylic acid derivative represented by the formula (1) could not be obtained in high yield and high purity.

As a result of an intensive investigation particularly on the reaction solvent, the present inventors found that a large amount of by-products other than the compound of the formula (1) was formed by reacting the compound of the formula (2) with the compound of the formula (3) in the presence of an ester-based solvent such as ethyl acetate and butyl acetate, the compound of the formula (1) could not be obtained in high yield, and extremely complex procedures were required for removing the by-products. The inventors have surprisingly found that the salicylic acid derivative of the formula (1) can be prepared in high yield and high purity by carrying out the reaction in the presence of the alcohol-based solvent.

The compound represented by the formula (2) can be prepared by known processes described, for example, in J. Prakt, Chem., 61, 532 (1900), J. Org. Chem., 19, 510 (1954), Japanese Laid-Open Patent Sho 57-26652, German Patent 3638364, and J. Chem. Soc., 2049 (1953).

For example, a 3-aminosalicylic acid derivative can be prepared by reducing 3-nitrosalicylic acid.

A 4-aminosalicylic acid derivative can be prepared by reacting a 3-aminophenol derivative with carbon dioxide in the presence of a base such as potassium carbonate, or by reducing 4-nitrosalicylic acid.

A 5-aminosalicylic acid derivative can be prepared by reacting a salicylic acid derivative with a diazonium salt and successively reducing the resulting diazonium compound.

A 6-aminosalicylic acid derivative can be prepared by reducing a 6-nitrosalicylic acid derivative.

Z in the formula (3) is a halogen atom, preferably a fluorine, chlorine or bromine atom, more preferably a chlorine atom.

The compound represented by the formula (3) can be prepared by known processes described, for example, in Methoden Der Organishen Chemie, 8, 1018 (1952); J. Am. Chem. Soc., 72, 1254 (1950); Angewandte Chemie, International Edition, 4, 281 (1967); and Chem. Review, 73, 75 (1973).

For example, the compound wherein Z in the formula (3) is chlorine can be prepared by reacting phosgene or thiophosgene with alcohols, phenols, thiols or thiophenols.

The alcohol-based solvents which can be used for the process of the invention is preferably alcohols having from 1 to 8 carbon atoms and includes, for example, methanol, ethanol, propanol, butanol, pentanol, heptanol, octanol, cyclohexanol, methyl cellosolve and ethyl cellosolve. These solvents can be used singly or as a mixture.

The process of the invention is characterized by reacting the compound of the formula (2) with the compound of the formula (3) in the presence of the alcohol-based solvent. The alcohol-based solvent can be used in combination with other organic solvents. In such cases, when the amount of the alcohol-based solvent is less than 10% by weight for the total amount of the solvents, reaction requires a long time or an unreacted compound of the formula (2) remains after the reaction. Accordingly, the amount of the alcohol-based solvent is preferably 10% by weight or more, more preferably 30% by weight or more, most preferably 50% by weight or more in the total amount of the solvents.

Other organic solvents which can be used in combination with the alcohol-based solvent include, for example, benzene, toluene, xylene, pentane, hexane, heptane, octane, cyclohexane and other hydrocarbon solvents; ethyl acetate, butyl acetate, amyl acetate and other ester solvents; diethyl ether, dioxane, tetrahydrofuran and other ether solvents; and dichloromethane, chloroform, dichloroethane, chlorobenzene, dichlorobenzene and other halogenated hydrocarbon solvents.

When the alcohol-based solvent has good compatibility with water as particularly in the case of methanol, ethanol and propanol, a mixture of the solvent with water can also be used. In view of the solubility of the compound represented by the formula (2), the amount of water is preferably 50% by weight or less, more preferably 30% by weight or less in the total weight of the solvent mixture.

No particular limitation is imposed upon the amount of the solvent. However, too much amount of the solvent is unfavorable in view of production efficiency and too small amount of the solvent requires a long reaction time, which is also unfavorable in view of production efficiency. The amount is preferably from 0.5 to 200 times by weight, more preferably from 1 to 100 times by weight for the amount of the compound represented by the formula (2).

The amount of the compound represented by the formula (3) is usually from 0.9 to 1.5 moles, preferably from 1 to 1.2 moles per mole of the compound represented by the formula (2).

The reaction temperature is usually from −20° C. to the boiling point of the solvent, preferably from 0° C. to the boiling point of the solvent.

The reaction time depends upon the reaction temperature and usually requires from several minutes to several hours. The progress of the reaction can be monitored with a known analytical means such as high performance liquid chromatography by persons skilled in the art.

By using such means, the reaction can also be terminated at a desired reaction rate, the reaction product is post treated and the salicylic acid derivative represented by the formula (1) can be isolated.

Even though the reaction is carried out in the absence of the base as a dehalogenating agent, the desired salicylic acid derivative can be obtained by the action of the compound of the formula (2) as a dehalogenating agent. However, the reaction is preferably carried out in the presence of the base. Exemplary bases which can be preferably used include sodium carbonate, potassium carbonate, sodium hydrogen carbonate, potassium hydrogen carbonate, sodium hydroxide, potassium hydroxide and other inorganic bases. These bases can be used singly or as a mixture.

After finishing the reaction, the reaction product can be isolated by usual post-treatment.

The salicylic acid derivative of the formula (1) which is prepared by the process of the invention has high purity of usually 98% or more. Purification to further high purity is preferred in order to use the salicylic acid derivative of the formula (1) or the metal salt of the derivative for the electron accepting compound of the heat-sensitive recording material. Further purification can be carried out, if desired, by known purification methods such as recrystallization and column chromatography.

The metal salt of the salicylic acid derivative represented by the formula (1) as an electron accepting compound in the heat-sensitive recording material of the invention comprises a salt of monovalent metals such as sodium, potassium and lithium and polyvalent metals of 2 to 4 valence. The metal salt can be prepared by the following process.

The metal salts of the salicylic acid derivative represented by the formula (1) of the invention, for example, the alkali metal salts such as sodium, potassium and lithium salt can be usually prepared by reacting the salicylic acid derivative of the formula (1) with an aqueous solution of alkali metal hydroxide, alkali metal carbonate and alkali metal hydrogen carbonate such as sodium hydroxide, potassium hydroxide, lithium hydroxide, sodium carbonate, potassium carbonate and sodium hydrogen carbonate.

In the metal salt of the salicylic acid derivative of the formula (1), the salt of metals having 2, 3 and 4 valence is a novel compound. Such polyvalent metal salt of the salicylic acid derivative is difficultly soluble or insoluble in water and usually prepared by a double decomposition reaction of an aqueous solution of the alkali metal salt of the salicylic acid derivative represented by the formula (1) with an aqueous solution of corresponding water soluble compound of metal having 2, 3 or 4 valence. The double decomposition reaction can be carried out by heating or in the presence of a solvent.

In the double decomposition, the aqueous solution of the alkali metal salt of the salicylic acid derivative represented by the formula (1) can also be used by mixing two or more aqueous solutions individually containing an alkali metal salt of a different salicylic acid derivative represented by the formula (1).

For example, a mixture of aqueous solutions individually containing alkali-metal 4-(n-butyloxycarbonylamino)salicylate and alkali-metal 4-(n-octyloxycarbonylamino)salicylate, or a mixture of aqueous solutions individually containing alkali-metal 4-(phenyloxycarbonylamino)salicylate and alkali-metal 5-(cyclohexyloxycarbonylamino)salicylate can also be used in the invention for the preparation of metal salts having 2, 3 or 4 valence. The mixture of the polyvalent metal salts thus prepared can be suitably used for the electron accepting compound of the heat-sensitive recording material of the invention.

The above water soluble metal compounds include, for example, zinc sulfate, magnesium sulfate, calcium sulfate, aluminum sulfate and other sulfates; zinc chloride, magnesium chloride, calcium chloride, barium chloride, nickel chloride, cobalt chloride, aluminum chloride and other chlorides; and zinc acetate, manganese acetate and other acetates.

The metal salt of the salicylic acid derivative which is prepared as above sometimes forms solvate such as hydrate depending upon preparation conditions. The solvate is also suitable as the electron accepting compound in the heat-sensitive recording material of the invention. The solvate can of course be desolvated by known means such as drying to prepare the metal salt of the salicylic acid derivative which does not contain water or other solvents. Such a desolvated metal salt of the salicylic acid derivative can of course be used for the electron accepting compound in the heat-sensitive recording material of the invention.

The heat-sensitive recording material of the invention is prepared as illustrated below by using the above salicylic acid derivative of the formula (1) and/or the metal salt of said derivative for the electron accepting compound.

The salicylic acid derivative represented by the formula (1) and the metal salt of the salicylic acid derivative can be used singly or as a mixture of the derivative, a mixture of the metal salt of said derivative, or a mixture of the derivative and the metal salt of said derivative.

In the heat-sensitive recording material of the invention, the salicylic acid derivative of the formula (1) and/or the metal salt of said derivative are used as the electron accepting compound. The electron accepting compound and the color forming, electron donating compound are used in an amount of usually from 50 to 700 parts by weight, preferably from 100 to 500 parts by weight of the electron accepting compound (salicylic acid derivative and/or the metal salt thereof) for 100 parts by weight of the electron donating compound.

The color forming, electron donating compounds which are colorless or pale colored and can be used for the heat-sensitive recording material of the invention include, for example, triarylmethane compounds, diarylmethane compounds, rhodamine-lactam compounds, fluoran compounds, indolylphthalide compounds, pyridine compounds, spiro compounds and fluorene compounds.

Practical electron donating compounds will be illustrated below.

The triarylmethane compounds include, for example, 3,3-bis(4-dimethylaminophenyl)-6-dimethylaminophthalide [crystal violet lactone], 3,3-bis(4-dimethylaminophenyl)phthalide, 3-(4-dimethylaminophenyl)-3-(1,3-dimethylindol-3-yl)phthalide, 3-(4-dimethylaminophenyl)-3-(2-methylindol-3-yl)phthalide, 3,3-bis(9-ethylcarbazole-3-yl)-6-dimethylaminophthalide, 3-(4-dimethylaminophenyl)-3-(1-methylpyrrol-3-yl)-6-dimethylaminophthalide, and 3,3-bis[2,2-bis(4-dimethylaminophenyl)ethenyl-4,5,6,7-tetrachlorophthalide.

Diarylmethane compounds include, for example, 4,4-bis-dimethylaminobenzhydrin benzyl ether, N-halophenylleucoauramine, and N-2,4,5-trichlorophenylleucoauramine.

Rhodamine-lactam compounds include, for example, rhodamine-B-anilinolactam, rhodamine-(4-nitroanilino)lactam, and rhodamine-B-(4-chloroanilino)lactam.

Fluoran compounds include, for example, 3,6-dimethoxyfluoran, 3-dimethylamino-7-methoxyfluoran, 3-diethylamino-6-methoxyfluoran, 3-diethylamino-7-methoxyfluoran, 3-diethylamino-7-chlorofluoran, 3-diethylamino-6-methyl-7-chlorofluorane, 3-diethylamino-6,7-dimethylfluoran, 3-N-cyclohexyl-N-n-butylamino-7-methylfluoran, 3-diethylamino-7-dibenzylaminofluoran, 3-diethylamino-7-octylaminofluoran, 3-diethylamino-7-di-n-hexylaminofluoran, 3-diethylamino-7-anilinofluoran, 3-diethylamino-7-(2-chloroanilino)fluoran, 3-diethylamino-7-(3-chloroanilino)fluoran, 3-diethylamino-7-(2,3-dichloroanilino)fluoran, 3-diethylamino-7-(3-trifluoromethylanilino)fluoran, 3-di-n-butylamino-7-(2-chloroanilino)fluoran, 3-diethylamino-6-chloro-7-anilinofluoran, 3-di-n-butylamino-6-chloro-7-anilinofluoran, 3-diethylamino-6-methoxy-7-anilinofluoran, 3-di-n-butylamino-6-ethoxy-7-anilinofluoran, 3-pyrrolidino-6-methyl-7-anilinofluoran, 3-morpholino-6-methyl-7-anilinofluoran, 3-dimethylamino-6-methyl-7-anilinofluoran, 3-diethylamino-6-methyl-7-anilinofluoran, 3-di-n-butylamino-6-methyl-7-anilinofluoran, 3-di-n-pentylamino-6-methyl-7-anilinofluoran, 3-di-n-octylamino-6-methyl-7-anilinofluoran, 3-N-ethyl-N-methylamino-6-methyl-7-anilinofluoran, 3-N-n-propyl-N-methylamino-6-methyl-7-anilinofluoran, 3-N-n-propyl-N-ethylamino-6-methyl-7-anilinofluoran, 3-N-isopropyl-N-methylamino-6-methyl-7-anilinofluoran, 3-N-n-butyl-N-methylamino-6-methyl-7-anilinofluoran, 3-N-n-butyl-N-ethylamino-6-methyl-7-anilinofluoran, 3-N-n-butyl-N-n-propylamino-6-methyl-7-anilinofluoran, 3-N-isobutyl-N-methylamino-6-methyl-7-anilinofluoran, 3-N-isobutyl-N-ethylamino-6-methyl-7-anilinofluoran, 3-N-isopentyl-N-ethylamino-6-methyl-7-anilinofluoran, 3-N-n-hexyl-N-ethylamino-6-methyl-7-anilinofluoran, 3-N-n-octyl-N-ethylamino-6-methyl-7-anilinofluoran, 3-N-cyclohexyl-N-methylamino-6-methyl-7-anilinofluoran, 3-N-cyclohexyl-N-n-propylamino-6-methyl-7-anilinofluoran, 3-N-cyclohexyl-N-n-butylamino-6-methyl-7-anilinofluoran, 3-N-cyclohexyl-N-n-pentylamino-6-methyl-7-anilinofluoran, 3-N-cyclohexyl-N-n-hexylamino-6-methyl-7-anilinofluoran, 3-N-cyclohexyl-N-n-heptylamino-6-methyl-7-anilinofluoran, 3-N-cyclohexyl-N-n-octylamino-6-methyl-7-anilinofluoran, 3-N-cyclohexyl-N-n-decylamino-6-methyl-7-anilinofluoran, 3-N-2'-methoxyethyl-N-methylamino-6-methyl-7-anilinofluoran, 3-N-2'-methoxyethyl-N-ethylamino-6-methyl-7-anilinofluoran, 3-N-2'-methoxyethyl-N-isobutylamino-6-methyl-7-anilinofluoran, 3-N-2'-ethoxyethyl-N-methylamino-6-methyl-7-anilinofluoran, 3-N-2'-ethoxyethyl-N-ethylamino-6-methyl-7-anilinofluoran, 3-N-3'-methoxypropyl-N-methylamino-6-methyl-7-anilinofluoran, 3-N-3'-methoxypropyl-N-ethylamino-6-methyl-7-anilinofluoran, 3-N-3'-ethoxypropyl-N-methylamino-6-methyl-7-anilinofluoran, 3-N-3'-ethoxypropyl-N-ethylamino-6-methyl-7-anilinofluoran, 3-N-2'-tetrahydrofurfuryl-N-ethylamino-6-methyl-7-anilinofluoran, 3-N-(4'-methylphenyl)-N-ethylamino-6-methyl-7-anilinofluoran, 3-diethylamino-6-ethyl-7-anilinofluoran, 3-diethylamino-6-methyl-7-(3'-methylphenylamino)-fluoran, 3-diethylamino-6-methyl-7-(2',6'-dimethylphenylamino)fluoran, 3-di-n-butylamino-6-methyl-7-(2',6'-dimethylphenylamino)fluoran, 3-di-n-butylamino-7-(2',6'-dimethylphenylamino)fluoran, 2,2-bis[4'-(3-N-cyclohexyl-N-methylamino-6-methylfluoran-7-ylaminophenyl]propane, and 3-[4'-(4-phenylaminophenyl)aminophenyl]amino-6-methyl-7-chlorofluoran.

Indolylphthalide compounds include, for example, 3,3-bis(1-ethyl-2-methylindole-3-yl)phthalide, 3,3-bis(1-octyl-2-methylindole-3-yl)phthalide, 3-(2-ethoxy-4-diethylaminophenyl)-3-(1-ethyl-2-methylindole-3-yl)phthalide, 3-(2-ethoxy-4-dibutylaminophenyl)-3-(1-ethyl-2-methylindole-3-yl) phthalide, and 3-(2-ethoxy-4-diethylaminophenyl)-3-(1-octyl-2-methylindole-3-yl) phthalide.

Pyridine compounds include, for example, 3-(2-ethoxy-4-diethylaminophenyl)-3-(1-octyl-2-methylindole-3-yl)-4 or 7-azaphthalide, 3-(2-ethoxy-4-diethylaminophenyl)-3-(1-ethyl-2-methylindole-3-yl)-4 or 7-azaphthalide, 3-(2-hexyloxy-4-diethylaminophenyl)-3-(1-ethyl-2-methylindole-3-yl)-4 or 7-azaphthalide, 3-(2-ethoxy-4-diethylaminophenyl)-3-(1-ethyl-2-phenylindole-3-yl)-4 or 7-azaphthalide, and 3-(2-butoxy-4-diethylaminophenyl)-3-(1-ethyl-2-phenylindole-3-yl)-4 or 7-azaphthalide.

Spiro compounds include, for example, 3-methyl-spiro-dinaphthopyran, 3-ethyl-spiro-dinaphthopyran, 3-phenyl-spiro-dinaphthopyran, 3-benzyl-spiro-dinaphthopyran, 3-methyl-naphtho-(3-methoxybenzo)spiropyran, and 3-propyl-spiro-dibenzopyran.

Fluorene compounds include, for example, 3',6',-bis(-diethylamino)-5-diethylaminospiro(isobenzofuran-1,9'-fluorene)-3-one, and 3',6',-bis(diethylamino)-7-diethylamino-2-methylspiro(1,3-benzoxazine-4,9'-fluorene).

These color forming, electron donating compounds can be used singly, or as a mixture in order to control color tone of developed image or to obtain multi-colored heat-sensitive recording materials.

The heat-sensitive recording material of the invention is characterized by comprising as the electron accepting compound one or more salicylic acid derivatives of the formula (1) and/or the metal salts of said derivatives. Other electron accepting compounds can be simultaneously used in the range giving no adverse effect on the desired properties of the heat-sensitive recording material of the invention.

In such a case, the proportion of the salicylic acid derivative represented by the formula (1) and/or the metal salt of the derivative in the total electron accepting compounds is usually 20% by weight or more, preferably 40% by weight or more, most preferably 60% by weight or more.

Other electron accepting compounds which can be used in combination with the salicylic acid derivative of the formula (1) and/or the metal salt of the derivative include, for example, phenol derivatives, organic acids and their metal salts, complexes, urea derivatives and other organic electron accepting compounds; and acid clay and other inorganic electron accepting compounds.

Practical examples of preferred electron accepting compounds include organic electron accepting compounds such as 4-tert-butylphenol, 4-tert-octylphenol, 4-phenylphenol, 1-naphthol, 2-naphthol, hydroquinone, resorcinol 4-tert-octylcatechol, 2,2'-dihydroxybiphenyl, 4,4'-dihydroxydiphenyl ether, 2,2-bis(4'-hydroxyphenyl)propane [bisphenol A], 1,1-bis(4'-hydroxyphenyl)cyclohexane, 2,2-bis(4'-hydroxy-3'-methylphenyl)propane, 1,4-bis(4'-hydroxycumyl)benzene, 1,3,5-tris(4'-hydroxycumyl)benzene, 4,4-(m-phenylenediisopropylidene)bisphenol, 4,4-(p-phenylenediisopropylidene)bisphenol, ethyl 2,2-bis(4'-hydroxyphenyl)acetate, n-butyl 4,4-(4'-hydroxyphenyl)pentanoate, benzyl 4-hydroxybenzoate, phenethyl 4-hydroxybenzoate, phenoxyethyl 2,4-dihydroxybenzoate, dimethyl 4-hydroxyphthalate, n-propyl gallate, n-octyl gallate, n-dodecyl gallate, n-octadecyl gallate, hydroquinone monobenzyl ether, bis(3-methyl-4-hydroxyphenyl)sulfide, bis(2-methyl-4-hydroxyphenyl)sulfide, bis(3-phenyl-4-hydroxyphenyl)sulfide, bis(3-cyclohexyl-4-hydroxyphenyl)sulfide, bis(4-hydroxyphenyl)sulfoxide, bis(4-hydroxyphenyl)sulfone, bis-(3-allyl-4-hydroxyphenyl)sulfone, 2,4'-dihydroxydiphenyl sulfone, 4-hydroxy-4'-methyldiphenyl sulfone, 4-hydroxy-4'-chlorodiphenyl sulfone, 4-hydroxy-4'-n-propoxydiphenyl sulfone, 4-hydroxy-4'-isopropoxydiphenyl sulfone, 4-hydroxy-4'-n-butoxydiphenyl sulfone, 3,4-dihydroxy-4'-methyldiphenyl sulfone, 2,4-dihydroxydiphenyl sulfone, 2-methoxy-4'-hydroxydiphenyl sulfone, 2-ethoxy-2'-hydroxydiphenyl sulfone, bis(2-hydroxy-5-tert-butylphenyl)sulfone, bis(2-hydroxy-5-chlorophenyl)sulfone, 4-hydroxybenzophenone, 2,4-dihydroxybenzophenone, 1,7-di(4-hydroxyphenylthio)-3,5-dioxaheptane, 1,5-di(4-hydroxyphenylthio)-3-oxapentane, and other phenol derivatives, salicylic acid, 3-isopropylsalicylic acid, 3-cyclohexylsalicylic acid, 3,5-di-tert-butylsalicylic acid, 3,5-di-α-methylbenzylsalicylic acid, 3-methyl-5-α-methylbenzylsalicylic acid, 4-[2'-(4-methoxyphenyloxy)ethyloxy]salicylic acid, 2-hydroxy-3-naphthoic acid, 2-hydroxy-6-naphthoic acid, monobenzyl phthalate, monophenyl phthalate, 4-nitrobenzoic acid, 3-nitrobenzoic acid, 2-nitrobenzoic acid, 4-chlorobenzoic acid and other organic acid and metal salts thereof such as salts of nickel, zinc, aluminum and calcium, zinc thiocyanate-antipyrin complex, molybdenic acid-acetylacetone complex and other complexes, phenylthiourea, di(3-trifluoromethylphenyl)thiourea, 1,4-di(3'-chlorophenyl)-3-thiosemicarbazide and other urea derivatives; and inorganic electron accepting compounds such as acid clay, attapulgite, activated clay, aluminum chloride, zinc chloride and zinc bromide.

These electron accepting compounds can be used singly or as a mixture.

Further, a heat fusible compound which has a melting point of from 70° to 150° C., preferably from 80° to 130° C. can be added as a sensitizer to the heat-sensitive recording material of the invention in order to enhance developing sensitivity and conform to high speed recording.

The heat fusible compound is used in an amount of usually from 10 to 700 parts by weight, preferably from 20 to 500 parts by weight for 100 parts by weight of the color forming, electron donating compound.

Exemplary heat fusible compounds which can be used include capronamide, capramide, palmitamide, stearamide, oleamide, stearyl urea, stearanilide, N-ethylcarbazole, 4-methoxydiphenylamine and other nitrogen containing compounds; benzyl 4-benzyloxybenzoate, phenyl 2-naphthoate, phenyl 1-hydroxy-2-naphthoate, dibenzyl oxalate, di(4-methylbenzyl)oxalate, di(4-chlorobenzyl)oxalate, diphenacyl glutarate, di(4-methylphenyl)carbonate, dibenzyl terephthalate and other ester compounds; 4-benzylbiphenyl, m-terphenyl, fluorene, fluoranthene, 2,6-diisopropylnaphthalene, 3-benzylacenaphthene and other hydrocarbon compounds; 2-benzyloxynaphthalene, 2-(4'-methylbenzyloxy)naphthalene, 1,4-diethoxynaphthalene, 1,2-diphenoxyethane, 1,2-bis (3'-methylphenoxy)ethane, 1-phenoxy-2-(4'-ethylphenoxy)ethane, 1-(4'-methoxyphenoxy)-2-phenoxyethane, 1-(4'-methoxyphenoxy)-2-(3'-methylphenoxy)ethane, 1-(4'-methoxyphenoxy)-2-(2'-methylphenoxy)ethane, 4-(4'-methylphenoxy)biphenyl, 1,4-bis(2'-chlorobenzyloxy)benzene, 4,4'-di-n-butoxydiphenylsulfone, 1,2-diphenoxybenzene, 1,4-bis(2'-chlorophenoxy)benzene, 1,4-bis(4'-methylphenoxy)benzene, 1,4-bis(3'-methylphenoxymethyl)benzene, 4-chlorobenzyloxy-(4'-ethoxybenzene), 4,4'-bis(phenoxy)diphenyl ether, 4,4'-bis(phenoxy)diphenyl thioether, 1,4-bis(4'-benzylphenoxy)benzene, 1,4-bis[(4'-methylphenyloxy)methoxymethyl]benzene and other ether compounds.

These heat fusible compounds can be used singly or as a mixture.

The heat-sensitive recording material of the invention can be prepared by known methods without using a specific method.

Generally, the color-forming, electron donating compound, the salicylic acid derivative of the formula (1) and/or the metal salt of the derivative and other ingredients are individually pulverized and dispersed in a water soluble binder with a ball mill, sand mill, horizontal sand mill, attrition mill, colloid mill and other means. The dispersions thus obtained have a particle size of usually 3 μm or less, preferably 1.5 μm or less. The dispersions are successively mixed to prepare coating liquid for a recording layer.

Inorganic metal compounds such as zinc oxide, zinc carbonate, calcium carbonate, magnesium carbonate, barium carbonate, barium sulfate, titanium oxide, aluminum hydroxide and magnesium hydroxide are sometimes used as metal pigments. In some cases, the metal pigments are preferably dispersed in combination with the salicylic acid derivative of the formula (1) and/or the metal salt of the derivative. The heat-sensitive recording materials having the higher storage stability of a developed color image can be obtained in these cases.

Practical examples of the water soluble binders include polyvinyl alcohol, sulfonated polyvinyl alcohol, hydroxyethyl cellulose, hydroxypropyl cellulose, epichlorohydrin modified polyamide, ethylene-maleic anhydride copolymer, styrene-maleic anhydride copolymer, isobutylene maleic anhydride copolymer, polyacrylic acid, polyacrylamide, methylol modified polyacrylamide, starch derivative, casein, gelatin, methylcellulose, carboxymethylcellulose, gum arabic and carboxyl modified polyvinyl alcohol.

Further, pigments, water insoluble binders, metallic soaps, wax, surfactants, ultraviolet absorbers, hindered phenols and anti-foaming agents are added, if desired, in the recording layer of the heat-sensitive recording material of the invention.

Exemplary pigments include zinc oxide, zinc carbonate, calcium carbonate, magnesium carbonate, barium carbonate, barium sulfate, titanium dioxide, talc, agalmatolite, kaolin, diatomaceous earth, aluminum hydroxide, magnesium hydroxide, alumina, silica, amorphous silica, urea-formaldehyde filler, polyethylene particulate and cellulose filler.

Synthetic rubber latex and synthetic resin emulsion such as styrene-butadiene rubber latex, acrylonitrile-butadiene rubber latex, methyl acrylate-butadiene rubber latex and polyvinyl acetate emulsion are generally known as water insoluble binders, and can also be used, if desired.

Metallic soaps which can be used are metal salts of higher fatty acids and include, for example, zinc stearate, calcium stearate, aluminum stearate and zinc oleate.

Exemplary wax includes, paraffin wax, microcrystalline wax, carboxy modified paraffin wax, carnauba wax, polyethylene wax, polystyrene wax, candelilla wax, montane wax and higher fatty acid esters.

Exemplary surfactants include alkali metal salts of sulfosuccinic acid such as sodium di(n-hexyl)sulfosuccinate and sodium di(2-ethylhexyl)sulfosuccinate, and fluorine-containing surfactants.

Exemplary ultraviolet absorbers include cinnamic acid derivatives, benzophenone derivatives and benzotriazolylphenol derivatives.

Hindered phenols are preferably phenol derivatives having a branched alkyl group on one or more ortho-positions to a phenolic hydroxyl group. Exemplary hindered phenols include: 1,1,3-tris(2-methyl-4-hydroxy-5-tert-butylphenyl)butane, 1,1,3-tris(2-methyl-4-hydroxy-5-cyclohexylphenyl)butane, 1,1,3-tris(2-ethyl-4-hydroxy-5-tert-butylphenyl)butane, 1,1,3-tris(3,5-di-tert-butyl-4-hydroxyphenyl)butane, 1,1,3-tris(2-methyl-4-hydroxy-5-tert-butylphenyl)propane, 2,2'-methylene-bis(6-tert-butyl-4-methylphenol), 2,2'-methylene-bis(6-tert-butyl-4-ethylphenol), 1,3,5-trimethyl-2,4,6-tris(3,5-di-tert-butyl-4-hydroxybenzyl)-benzene, 1,3,5-tris(4-tert-butyl-3-hydroxy-2,6-dimethylbenzyl)-isocyanuric acid, 1,3,5-tris(4-tert-butyl-3-hydroxy-2-methyl-6-ethylbenzyl)-isocyanuric acid, and bis(2-methyl-4-hydroxy-5-tert-butylphenyl)sulfide.

No particular restriction is imposed upon the preparation method of the recording layer in the heat-sensitive recording material of the invention. Conventionally known techniques can be used.

For example, the coating liquid of the heat-sensitive recording layer is applied on a substrate with a suitable coating device such as an air knife coater, blade coater, bar coater, gravure coater, curtain coater and wire bar, and successively dried to form a recording layer.

No particular limitation is placed on the amount of the coating liquid. The amount is usually from 1.5 to 12 g/m$^2$, preferably from 2.5 to 10 g/m$^2$ on dry weight.

The substrate which can be used is paper, plastic sheet and synthetic paper.

If desired, a protective layer can be furnished on the surface and/or the back side of the heat-sensitive recording layer, or an undercoating layer can of course be furnished between the substrate and the heat-sensitive recording layer. Tackifying and other known processing techniques can also be applied to the preparation of the heat-sensitive recording material in the invention.

The invention will hereinafter be illustrated further in detail by way of preparation examples and examples. However, these examples are not to be construed to limit the scope of the invention. In these preparation examples and examples, percent means percent by weight unless otherwise noted.

PREPARATION EXAMPLES 1

Preparation of Compound No. 77

To 700 ml of methanol suspended 153 g of 4-aminosalicylic acid and 84 g of sodium hydrogen carbonate, 193 g of n-octylchloroformate was dropwise added over 2 hours at room temperature. After finishing dropwise addition, the mixture was further stirred for 2 hours at room temperature. An aqueous solution containing 30 g of concentrated hydrochloric acid and 1200 ml of water was added to the reaction mixture. Precipitated crystals were filtered and dried to obtain 300 g of desired 4-(n-octyloxycarbonylamino)salicylic acid as colorless crystals. Yield was 97%.

Melting point was 157-159° C. Mass spectrum (EI): 309(M+)

IR absorption spectrum (KBr): 3360, 1720, 1640 and 1620 cm$^{-1}$

Purity of the product was 99% (area ratio) by high performance liquid chromatography.

COMPARATIVE PREPARATION EXAMPLE 1

To an aqueous solution dissolved 153 g of 4-aminosalicylic acid and 170 g of sodium hydrogen carbonate in 2200 ml of water, 193 g of n-octylchloroformate was dropwise added over 2 hours at room temperature. After finishing dropwise addition, the mixture was further stirred for 5 hours at room temperature. An aqueous solution containing 30 g of concentrated hydrochloric acid and 1200 ml of water was added to the reaction mixture. Precipitated crystals were filtered and dried to obtain 148 g of desired 4-(n-octyloxycarbonylamino)salicylic acid as colorless crystals. Yield was 48%.

COMPARATIVE PREPARATION EXAMPLE 2

To 700 ml of butyl acetate suspended with 153 g of 4-aminosalicylic acid and 84 g of sodium hydrogen carbonate, 193 g of n-octylchloroformate was dropwise added over 2 hours at room temperature. After finishing dropwise addition, the mixture was further stirred for 2 hours. Successively, inorganic salt was filtered and butyl acetate was distilled from the filtrate under reduced pressure to obtain crystals.

The crystals were analyzed by high performance liquid chromatography and found to contain about 10% of unreacted 4-aminosalicylic acid, about 80% of desired 4-(n-octyloxycarbonylamino)salicylic acid and about 10% (area ratio) of by-product.

The crude product was purified by an aqueous methanol solution (50:50 v/v). As a result, unreacted 4-aminosalicylic acid could be removed, but the desired product still contained about 12% (area ratio) of the by-product.

PREPARATION EXAMPLES 2~28

Various salicylic acid derivatives represented by the formula (1) were prepared by carrying out the same procedures described in Preparation Example 1 except that n-octylchloroformate was replaced by chloroformate compounds and alcohols which are illustrated in Table 1.

Any salicylic acid derivatives thus prepared had yield of 96% or more and purity of 99% or more.

TABLE 1

| Preparation Example | Chloroformate compound | Alcohol | Salicylic acid derivative |
|---|---|---|---|
| 2 | methyl-chloroformate | MeOH | compound No. 66 mp. 198~200° C. |
| 3 | ethyl-chloroformate | MeOH | compound No. 67 mp. 208~210° C. |
| 4 | n-propyl-chloroformate | MeOH-toluene (20:80) | compound No. 68 mp. 190~192° C. |
| 5 | n-butyl-chloroformate | MeOH—H₂O (80:20) | compound No. 70 mp. 159~161° C. |
| 6 | isobutyl-chloroformate | MeOH | compound No. 71 mp. 185~186° C. |
| 7 | n-pentyl-chloroformate | MeOH | compound No. 73 mp. 166~168° C. |
| 8 | n-hexyl-chloroformate | isopropanol | compound No. 75 mp. 165~167° C. |
| 9 | n-heptyl-chloroformate | isobutanol | compound No. 76 mp. 156~158 ° C. |
| 10 | 2-ethylhexyl-chloroformate | MeOH | compound No. 78 mp. 133~135° C. |
| 11 | n-nonyl-chloroformate | MeOH | compound No. 79 mp. 157~159° C. |
| 12 | n-decyl-chloroformate | MeOH | compound No. 80 mp. 158~160° C. |
| 13 | n-undecyl-chloroformate | EtOH | compound No. 81 mp. 155~157° C. |
| 14 | n-dodecyl-chloroformate | MeOH | compound No. 82 mp. 156~159° C. |
| 15 | n-tetradecyl-chloroformate | MeOH | compound No. 84 mp. 155~157° C. |
| 16 | n-hexadecyl-chloroformate | methyl-cellosolve | compound No. 86 mp. 153~155° C. |
| 17 | cyclohexyl-chloroformate | MeOH | compound No. 90 mp. 199~202° C. |
| 18 | 2-methoxyethyl-chloroformate | MeOH | compound No. 96 mp. 160~163° C. |
| 19 | 2-n-hexyloxy-ethyl-chloroformate | MeOH | compound No. 97 mp. 120~123° C. |
| 20 | 2-phenoxyethyl-chloroformate | MeOH | compound No. 105 mp. 186~189° C. |
| 21 | 2-(4'-methoxy-phenyl)oxy-ethylchloroformate | MeOH | compound No. 107 mp. 192~194° C. |
| 22 | benzyl-chloroformate | MeOH | compound No. 115 mp. 187~189° C. |
| 23 | phenyl-chloroformate | MeOH—AcOEt (20:80) | compound No. 119 p. 208~209° C. |
| 24 | 4-phenylphenyl-chloroformate | MeOH | compound No. 123 mp. 221~224° C. |
| 25 | 4-cumylphenyl-chloroformate | MeOH | compound No. 131 mp. 202~205° C. |
| 26 | 4-methoxy-phenyl-chloroformate | MeOH | compound No. 132 mp. 207~210° C. |
| 27 | 4-(4'-benzyloxy-cumyl)phenyl-chloroformate | MeOH | compound No. 138 mp. 206~210° C. |
| 28 | phenylthiol-chloroformate | MeOH | compound No. 163 mp. 300° C. or more |

PREPARATION EXAMPLE 29

Preparation of compound No. 188

To 700 ml of methanol suspended with 153 g of 5-aminosalicylic acid and 84 g of sodium hydrogen carbonate, 163 g of cyclohexylchloroformate was dropwise added over 2 hours at room temperature. After finishing dropwise addition, the mixture was further stirred for an hour at room temperature. Successively, an aqueous solution containing 30 g of concentrated hydrochloric acid and 1200 ml of water was added to the reaction mixture.

Precipitated crystals were filtered and dried to obtain 269 g of desired 5-(cyclohexyloxycarbonylamino)salicylic acid as colorless crystals.

Yield was 96%. Melting point was 260~262° C.

Purity of the product was 99% (area ratio) by high performance liquid chromatography.

PREPARATION EXAMPLES 30–54

Various salicylic acid derivatives represented by the formula (1) were prepared by carrying out the same procedures as described in Preparation Example 29 except that cyclohexylchloroformate was replaced by chloroformate compounds and alcohols which are illustrated in Table 2.

Any salicylic acid derivatives thus obtained had yield of 96% or more and purity of 99% or more.

TABLE 2

| Preparation Example | Chloroformate compound | Alcohol | Salicylic acid derivative |
|---|---|---|---|
| 30 | methyl-chloroformate | MeOH | compound No. 171 mp. 220~222° C. |
| 31 | ethyl-chloroformate | EtOH | compound No. 172 mp. 214~217° C. |
| 32 | n-propyl-chloroformate | MeOH-dichloroethane (50:50) | compound No. 173 mp. 199~202° C. |
| 33 | n-butyl-chloroformate | MeOH | compound No. 174 mp. 194~197° C. |
| 34 | iso-butyl-chloroformate | isopropanol | compound No. 175 mp. 200~202° C. |
| 35 | n-pentyl-chloroformate | MeOH | compound No. 176 mp. 184~186° C. |
| 36 | n-hexyl-chloroformate | n-butanol | compound No. 178 mp. 180~183° C. |
| 37 | n-heptyl-chloroformate | MeOH-isopropanol | compound No. 179 mp. 180~182° C. |
| 38 | n-octyl-chloroformate | MeOH | compound No. 180 mp. 180~182° C. |
| 39 | 2-ethylhexyl-chloroformate | MeOH | compound No. 181 mp. 147~149° C. |
| 40 | n-nonyl-chloroformate | MeOH | compound No. 182 mp. 177~180° C. |
| 41 | n-decyl-chloroformate | isopropanol | compound No. 183 mp. 179~181° C. |
| 42 | n-undecyl-chloroformate | MeOH | compound No. 184 mp. 178~180° C. |
| 43 | n-dodecyl-chloroformate | MeOH | compound No. 185 mp. 176~178° C. |
| 44 | n-tetradecyl-chloroformate | MeOH | compound No. 186 mp. 174~176° C. |
| 45 | n-hexadecyl-chloroformate | MeOH | compound No. 187 mp. 171~173° C. |
| 46 | 2-n-hexyloxyethyl-chloroformate | MeOH | compound No. 195 mp. 202~204° C. |
| 47 | 2-phenoxyethyl-chloroformate | MeOH | compound No. 200 mp. 210~214° C. |
| 48 | 2-(4'-methoxy-phenyl)oxyethyl-chloroformate | MeOH | compound No. 202 mp. 198~201° C. |
| 49 | benzyl-chloroformate | MeOH | compound No. 208 mp. 248~251° C. |
| 50 | phenyl-chloroformate | MeOH | compound No. 212 mp. 300° C. or more |
| 51 | 4-phenylphenyl-chloroformate | MeOH | compound No. 214 p. 255~259° C. |
| 52 | 4-cumylphenyl-chloroformate | MeOH | compound No. 218 mp. 164~167° C. |
| 53 | 4-methoxyphenyl-chloroformate | MeOH | compound No. 219 mp. 245~250° C. |
| 54 | 2,4-dimethyl-phenyl chloroformate | MeOH | compound No. 235 mp. 275~281° C. |

PREPARATION EXAMPLE 55

Preparation of zinc salt of compound No. 70

To 400 ml of an aqueous solution containing 8.4 g of sodium hydrogen carbonate, 25.3 g of 4-(n-butyloxycarbonylamino)salicylic acid was gradually added and dissolved at room temperature. The solution obtained was dropwise added to 200 ml of an aqueous solution containing 14.9 g of zinc sulfate 7 hydrate over 20 minutes at room temperature. After finishing dropwise addition, the mixture was further stirred for 30 minutes. Precipitated crystals were filtered, washed with water, and dried to obtain 26 g of desired zinc 4-(n-butyloxycarbonylamino)salicylate.

Melting point was 140~143° C. IR absorption spectrum (KBr): 1750 and 1630 cm$^{-1}$.

PREPARATION EXAMPLE 56

Preparation of zinc salt of compound No. 77

To a solution containing 8.4 g of sodium hydrogen carbonate, 400 ml of water and 600 ml of methanol, 31 g of 4-(n-octyloxycarbonylamino) salicylic acid was gradually add and dissolved at room temperature.

The solution obtained was dropwise added to 1200 ml of an aqueous solution containing 14.9 g of zinc sulfate 7 hydrate over an hour at room temperature. After finishing dropwise addition, the mixture was further stirred for 4 hours at room temperature. Precipitated crystals were filtered, washed with water and dried to obtain 33.3 g of desired zinc 4-(n-octyloxycarbonylamino)salicylate as colorless crystals.

Figure 1:
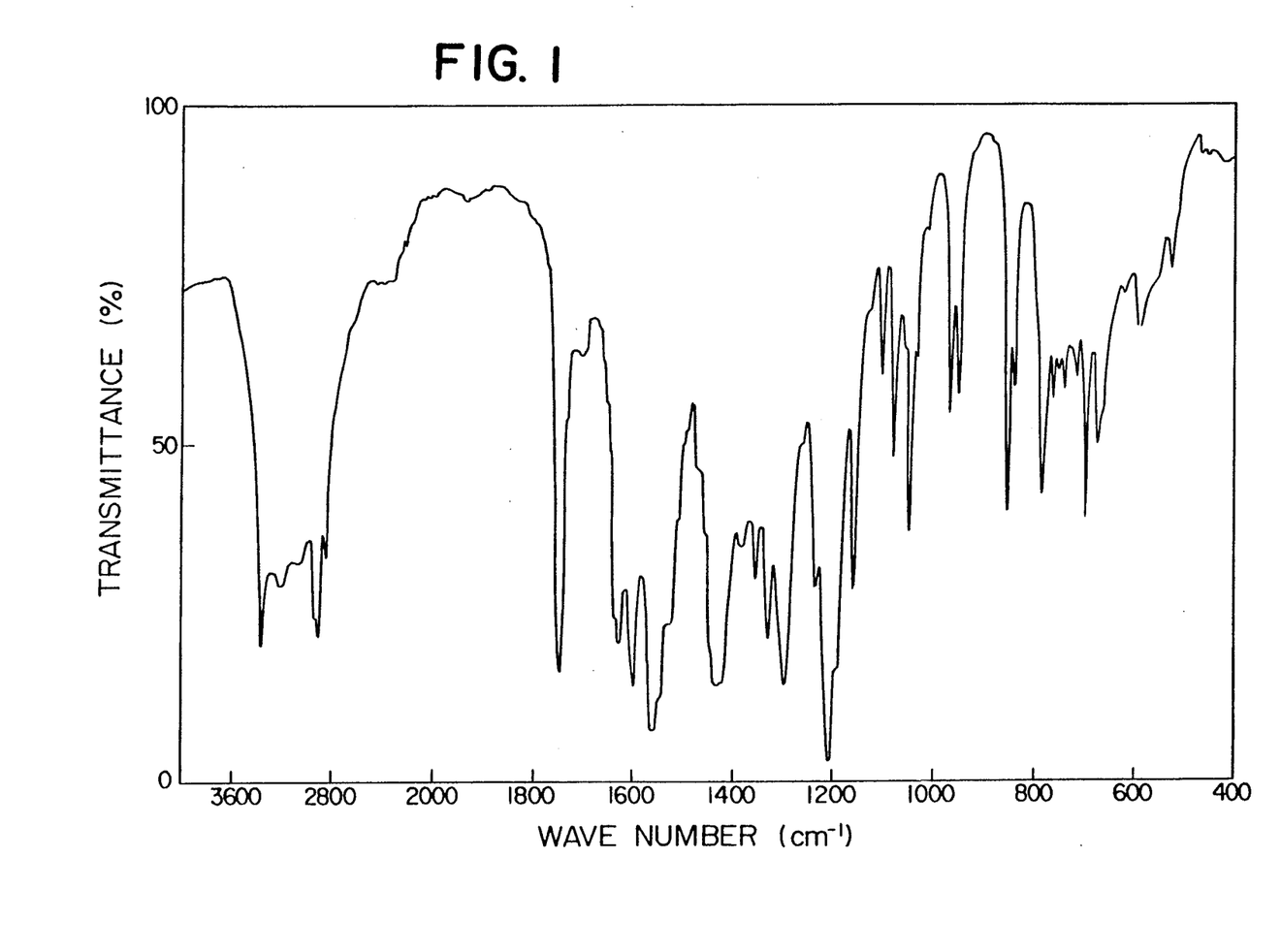
FIG. 1 is an IR absorption spectrum (KBr) on the zinc salt of Compound No. 77.

Melting point was 140~143° C. IR absorption spectrum (KBr) of the product is illustrated in FIG. 1.

PREPARATION EXAMPLE 57

Preparation of zinc salt of compound No. 80

Zinc 4-(n-decyloxycarbonylamino)salicylate was prepared by carrying out the same procedures as described in preparation example 56 except that 4-(n-octyloxycarbonylamino)salicylic acid was replaced by 4-(n-decyloxycarbonylamino)salicylic acid.

Figure 2:
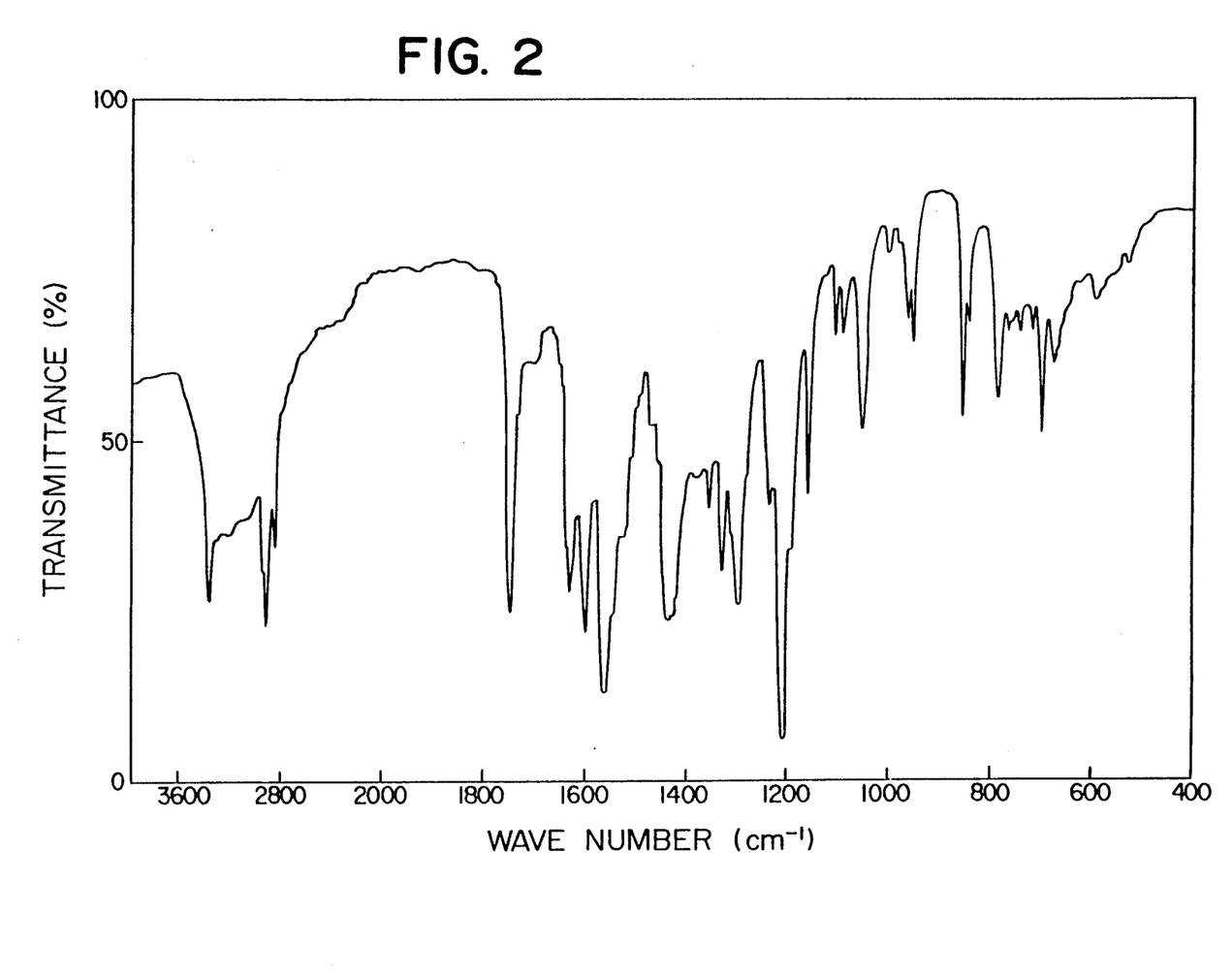
FIG. 2 is an IR absorption spectrum (KBr) on the zinc salt of Compound No. 80.

Melting point was 141~144° C. IR absorption spectrum (KBr) of the product is illustrated in FIG. 2.

PREPARATION EXAMPLE 58

Preparation of zinc salt of compound No. 82

Zinc 4-(n-dodecyloxycarbonylamino)salicylate was prepared by carrying out the same procedures as described in Preparation Example 56 except that 4-(n-octyloxycarbonylamino)salicylic acid is replaced by 4-(n-dodecyloxycarbonylamino)salicylic acid.

Melting point was 130~134° C. IR absorption spectrum (KBr): 1750 and 1630 cm$^{-1}$.

PREPARATION EXAMPLE 59

Preparation of zinc salt of compound No. 115

Zinc 4-(benzyloxycarbonylamino)salicylate was prepared by carrying out the same procedures as described in Preparation Example 56 except that 4-(n-octyloxycarbonylamino)salicylic acid was replaced by 4-(benzyloxycarbonylamino)salicylic acid.

Melting point was 300° C. or more.

PREPARATION EXAMPLE 60

Preparation of zinc salt of compound No. 119

Zinc 4-(phenyloxycarbonylamino)salicylate was prepared by carrying out the same procedures as described in Preparation Example 56 except that 4-(n-octyloxycarbonylamino)salicylic acid is replaced by 4-(phenyloxycarbonylamino)salicylic acid.

Melting point was 300° C. or more. IR absorption spectrum (KBr): 1760 and 1630 cm$^{-1}$.

PREPARATION EXAMPLE 61

Preparation of zinc salt of compound No. 188

Zinc 5-(cyclohexyloxycarbonylamino)salicylate was prepared by carrying out the same procedures as described in Preparation Example 56 except that 4-(n-octyloxycarbonylamino)salicylic acid was replaced by 5-(cyclohexyloxycarbonylamino)salicylic acid.

Melting point was 300° C. or more. IR absorption spectrum (KBr): 1690 and 1640 cm$^{-1}$.

PREPARATION EXAMPLE 62

Preparation of zinc salt of compound No. 202

Zinc 5-[2'-(4-methoxyphenyl)oxyethyloxycarbonylamino]salicylate was prepared by carrying out the same procedures as described in Preparation Example 56 except that 4-(n-octyloxycarbonylamino) salicylic acid was replaced by 5-[2'-(4-methoxyphenyl)oxyethyloxycarbonylamino]salicylic acid.

Melting point was 300° C. or more.

PREPARATION EXAMPLE 63

Preparation of nickel salt of compound No. 77

Nickel 4-(n-octyloxycarbonylamino)salicylate was prepared by carrying out the same procedures as described in Preparation Example 56 except that zinc sulfate 7 hydrate was replaced by nickel chloride 6 hydrate.

Melting point was 300° C. or more. IR absorption spectrum (KBr): 1710 and 1610 cm$^{-1}$.

PREPARATION EXAMPLE 64

Preparation of manganese salt of compound No. 77

Manganese 4-(n-octyloxycarbonylamino)salicylate was prepared by carrying out the same procedures as described in Preparation Example 56 except that zinc sulfate 7 hydrate was replaced by manganese acetate hydrate.

Melting point was 300° C. or more. IR absorption spectrum (KBr): 1720 and 1600 cm$^{-1}$.

PREPARATION EXAMPLE 65

Preparation of cobalt salt of compound No. 77

Cobalt 4-(n-octyloxycarbonylamino)salicylate was prepared by carrying out the same procedures as described in Preparation Example 56 except that zinc sulfate 7 hydrate was replaced by cobalt chloride 6 hydrate.

Melting point was 200~205° C.

PREPARATION EXAMPLE 66

Preparation of aluminum salt of compound No. 77

Aluminum 4-(n-octyloxycarbonylamino)salicylate was prepared by carrying out the same procedures as described in Preparation Example 56 except that zinc sulfate 7 hydrate was replaced by aluminum chloride.

Melting point was 190~195° C. IR absorption spectrum (KBr): 1720 and 1630 cm$^{-1}$.

PREPARATION EXAMPLE 67

Preparation of magnesium salt of compound No. 188

To 400 ml of an aqueous solution containing 4.0 g of sodium hydroxide, 27.9 g of 5-(cyclohexyloxycarbonylamino)salicylic acid was gradually added and dissolved at room temperature. The solution thus obtained was dropwise added over 20 minutes at room temperature to 200 ml of an aqueous solution containing 10.2 g of magnesium chloride 6 hydrate. After finishing dropwise addition, the mixture was further stirred for 30 minutes. Precipitated crystals were filtered, washed with water and dried to obtain 28 g of desired magnesium 5-(cyclohexyloxycarbonylamino)salicylate.

Melting point was 300° C. or more. IR absorption spectrum (KBr): 1690 and 1630 cm$^{-1}$.

PREPARATION EXAMPLE 63

Preparation of calcium salt of compound No. 188

Calcium 5-(cyclohexyloxycarbonylamino)salicylate was prepared by carrying out the same procedures as described in Preparation Example 67 except that magnesium chloride 6 hydrate was replaced by calcium chloride.

Melting point was 300° C. or more. IR absorption spectrum (KBr): 1690cm$^{-1}$.

PREPARATION EXAMPLE 69

Preparation of barium salt of compound No. 188

Barium 5-(cyclohexyloxycarbonylamino)salicylate was prepared by carrying out the same procedures as described in Preparation Example 67 except that magnesium chloride 6 hydrate was replaced by barium chloride 2 hydrate.

Melting point was 300° C. or more.

PREPARATION EXAMPLE 70

Preparation of nickel salt of compound No. 188

Nickel 5-(cyclohexyloxycarbonylamino)salicylate was prepared by carrying out the same procedures as described in Preparation Example 67 except that magnesium chloride 6 hydrate was replaced by nickel chloride 6 hydrate. Melting point was 300° C. or more.

The electron accepting compounds of the invention which was obtained in Preparation Examples will hereinafter be used for preparing heat-sensitive recording paper and the results of evaluating properties of the paper will be illustrated as examples.

In order to prepare heat-sensitive recording paper in each example, the components A, B, C and D having the following compositions were individually pulverized with a sand grinding mill to prepare dispersion having an average particle size of 1.5 μm or less

| (Composition of component A) | |
|---|---|
| Color forming, electron donating compound | 10 g |
| 10% Aqueous polyvinyl alcohol solution (Kuraray 117) | 10 g |
| Water | 80 g |
| total | 100 g |

| (Composition of component B) | |
|---|---|
| Electron accepting compound | 20 g |
| Precipitated calcium carbonate (Okutama Kogyo, TP-123) | 40 g |
| 10% Aqueous polyvinyl alcohol solution (Kuraray 117) | 60 g |
| Water | 130 g |
| total | 250 g |

| (Composition of component C) | |
|---|---|
| Electron accepting compound | 20 g |
| Precipitated calcium carbonate (Okutama Kogyo, TP-123) | 10 g |
| Zinc oxide | 30 g |
| 10% Aqueous polyvinyl alcohol solution (Kuraray 117) | 60 g |
| Water | 130 g |
| total | 250 g |

| (Composition of component D) | |
|---|---|
| Heat fusible compound (2-benzyloxynaphthalene) | 20 g |
| 10% Aqueous polyvinyl alcohol solution (Kuraray 117) | 10 g |
| Water | 220 g |
| total | 250 g |

Properties of each heat-sensitive recording paper was evaluated by the following methods.

(1) Storage stability test of an uncolored portion

Whiteness was measured immediately after coating with a color difference meter, Σ-80(Trade mark of Nippon Denshoku Co.) on the uncolored portion of each heat-sensitive recording paper which was prepared in the examples and comparative examples.

The heat-sensitive recording paper prepared in Comparative Examples 3, 4 and 5 was already soiled to gray immediately after coating. The moist heat resistance test and the oil resistance test were individually carried out and storage stability was evaluated after each test by measuring whiteness of the uncolored portion on the heat-sensitive recording paper.

The moist heat resistance test was carried out by storing each heat-sensitive recording paper at 40° C. in 90% relative humidity for 24 hours and successively measuring whiteness with a color difference meter. The oil resistance test was carried out by superposing a sheet of paper coated with capsules containing dioctyl phthalate upon each heat-sensitive recording paper, passing through press rolls, storing at 25° C. for a week and thereafter measuring the whiteness of the uncolored portion with a color difference meter.

A larger value indicates higher whiteness and illustrates excellent storage stability of the uncolored portion.

The writing utensils resistance test was carried out by writing on an uncolored portion with a fluorescent pen, allowing to stand at 25° C. for 72 hours and then visually observing the whiteness of the uncolored portion.

◯ indicates high whiteness without soil.

X indicates a dark gray soiled state.

(2) Storage stability test of a developed image

A developed color image having color density of 0.6 according to a Macbeth reflection densitometer TR-524 was formed on each heat-sensitive recording paper by using a color forming apparatus for heat-sensitive recording paper, TH-PMD (Trade mark of Okura Denki Co.)

The storage stability test was carried out by using the image developed recording paper thus obtained. The moist heat resistance test and oil resistance test were individually carried out and storage stability was evaluated by measuring the storage stability of developed color image on each recording paper after each test.

The moist heat resistance test was carried out by storing the image developed recording paper at 60° C. in 90% relative humidity for 24 hours and thereafter measuring the image density with a Macbeth reflection densitometer to calculate a residual rate of color image.

The oil resistance test was carried out by superposing the paper coated with capsules containing dioctyl phthalate upon each image developed recording paper, passing through press rolls, storing at 25 ° C. for a week and thereafter measuring the density of color image with a Macbeth reflection densitometer to calculate a residual rate of color image.

$$\text{Residual rate (\%)} = \frac{\text{density of color image after test}}{\text{original density of color image}(0.6)} \times 100$$

A larger value indicates higher storage stability of developed color image.

The writing utensils resistance test was carried out by writing on a colored portion of each image developed recording paper with a fluorescent pen, allowing to stand at 25 ° C. for 72 hours and then visually observing the residual rate of the colored portion.

⊙ No color fading was observed.
○ A little color fading was observed.
X Color fading was observed.

Results are illustrated in Table 7.

EXAMPLES 1~25

Mixtures composed of 100 g of component A, 250 g of component B, 250 g of component D and 23 g of 30% paraffin wax were coated on wood free paper so as to obtain dry coating weight of 5.0±0.5 g/m² and dried to obtain heat-sensitive recording paper.

Color forming, electron donating compounds in component A and electron accepting compounds in component B which were used in these examples are illustrated in Table 3.

Results of the storage stability test on the uncolored portion of resulting heat-sensitive recording paper are illustrated in Table 6. Results of the storage stability test on the developed color image are illustrated in Table 7.

TABLE 3

| Example | Color forming, electron donating compound | Electron accepting compound |
|---|---|---|
| 1 | 3-di-n-pentylamino-6-methyl-7-anilinofluoran | zinc salt of compound No. 68 |
| 2 | 3-di-n-butylamino-6-methyl-7-anilinofluoran | zinc salt of compound No. 70 |
| 3 | 3-di-n-butylamino-6-methyl-7-anilinofluoran | zinc salt of compound No. 76 |
| 4 | 3-di-n-butylamino-6-methyl-7-anilinofluoran | zinc salt of compound No. 77 |
| 5 | 3-N-isopentyl-N-ethylamino-6-methyl-7-anilinofluoran | manganese salt of compound No. 77 |
| 6 | 3-di-n-butylamino-6-methyl-7-anilinofluoran | zinc salt of compound No. 79 |
| 7 | 3-di-n-butylamino-6-methyl-7-anilinofluoran | zinc salt of compound No. 80 |
| 8 | 3-di-n-butylamino-6-methyl-7-anilinofluoran | zinc salt of compound No. 81 |
| 9 | 3-di-n-butylamino-6-methyl-7-anilinofluoran | zinc salt of compound No. 82 |
| 10 | 3-N-isopentyl-N-ethylamino-6-methyl-7-anilinofluoran | zinc salt of compound No. 84 |
| 11 | 3-N-3'-ethoxypropyl-N-ethylamino-6-methyl-7-anilinofluoran | zinc salt of compound No. 107 |
| 12 | 3-di-n-butylamino-6-methyl-7-anilinofluoran | zinc salt of compound No. 115 |
| 13 | 3-di-n-butylamino-6-methyl-7-anilinofluoran | zinc salt of compound No. 119 |
| 14 | 3-di-n-butylamino-6-methyl-7-anilinofluoran | zinc salt of compound No. 121 |
| 15 | 3-di-n-butylamino-6-methyl-7-anilinofluoran | zinc salt of compound No. 123 |
| 16 | 3-di-n-butylamino-6-methyl-7-anilinofluoran | zinc salt of compound No. 124 |
| 17 | 3-N-n-propyl-N-methylamino-6-methyl-7-anilinofluoran | zinc salt of compound No. 131 |
| 18 | 3-N-isobutyl-N-methylamino-6-methyl-7-anilinofluorane | zinc salt of compound No. 151 |
| 19 | 3-N-2'-methoxyethyl-N-isobutylamino-6-methyl-7-anilinofluoran | zinc salt of compound No. 163 |
| 20 | 3-N-isopentyl-N-ethylamino-6-methyl-7-anilinofluorane | zinc salt of compound No. 181 |
| 21 | 3-N-isopentyl-N-ethylamino-6-methyl-7-anilinofluorane | zinc salt of compound No. 188 |
| 22 | 3-di-n-butylamino-6-methyl-7-anilinofluoran | magnesium salt of compound No. 188 |
| 23 | 3-di-n-butylamino-6-methyl-7-anilinofluoran | nickel salt of compound No. 188 |
| 24 | 3-di-n-butylamino-6-methyl-7-anilinofluoran | zinc salt of compound No. 202 |
| 25 | 3-di-n-butylamino-6-methyl-7-anilinofluoran | zinc salt of compound No. 77 (50%) + compound No. 119 (50%) |

EXAMPLES 26~31

Mixtures composed of 100 g of component A, 250 g of component C, 250 g of component D and 23 g of 30% paraffin wax were coated on wood free paper so as to obtain dry coating weight of 5.0±0.5 g/m² and dried to obtain heat-sensitive recording paper.

Color forming, electron donating compounds in component A and electron accepting compounds in component C which were used in these examples are illustrated in Table 4.

Results of the storage stability test on the uncolored portion of resulting heat-sensitive recording paper are illustrated in Table 6. Results of the storage stability test on the developed color image are illustrated in Table 7.

TABLE 4

| Example | Color forming, electron donating compound | Electron accepting compound |
|---|---|---|
| 26 | 3-di-n-butylamino-6-methyl-7-anilinofluoran | compound No. 70 |
| 27 | 3-di-n-butylamino-6-methyl-7-anilinofluoran | zinc salt of compound No. 77 |
| 28 | 3-di-n-pentylamino-6-methyl-7-anilinofluoran | compound No. 79 |
| 29 | 3-di-n-butylamino-6-methyl-7-anilinofluoran | compound No. 80 |
| 30 | 3-dimethylamino-6-methyl-7-anilinofluoran | compound No. 119 |
| 31 | 3-di-n-butylamino-6-methyl- | compound No. 125 |

TABLE 4-continued

| Example | Color forming, electron donating compound | Electron accepting compound |
|---|---|---|
| | 7-anilinofluoran | |

COMPARATIVE EXAMPLES 1~8

Mixtures composed of 100 g of component A, 250 g of component B, 250 g of component D and 23 g of 30% paraffin wax were coated on wood free paper so as to obtain dry coating weight of $5.0\pm0.5$ g/m$^2$ and dried to obtain heat-sensitive recording paper.

Color forming, electron donating compounds in component A and electron accepting compounds in component B which were used in these comparative examples are illustrated in Table 5.

Results of the storage stability test on the uncolored portion of resulting heat-sensitive recording paper are illustrated in Table 6. Results of the storage stability test on the developed color image are illustrated in Table 7.

TABLE 5

| Comparative Example | Color forming, electron donating compound | Electron accepting compound |
|---|---|---|
| 1 | 3-di-n-butylamino-6-methyl-7-anilinofluoran | bisphenol A |
| 2 | 3-di-n-butylamino-6-methyl-7-anilinofluoran | benzyl 4-hydroxybenzoate |
| 3 | 3-N-isopentyl-N-ethylamino-6-methyl-7-anilinofluoran | zinc 3,5-di-tert-butylsalicylate |
| 4 | 3-N-isobutyl-N-methylamino-6-methyl-7-anilinofluoran | zinc 3,5-di(α-methylbenzyl)-salisylate |
| 5 | 3-di-n-butylamino-6-methyl-7-anilinofluoran | zinc 4-n-hexyl-oxysalicylate |
| 6 | 3-di-n-butylamino-6-methyl-7-anilinofluoran | zinc 4-n-phenyl-acetylamino-salicylate |
| 7 | 3-di-n-butylamino-6-methyl-7-anilinofluoran | zinc 4-benzoyl-aminosalicylate |
| 8 | 3-di-n-butylamino-6-methyl-7-anilinofluoran | zinc 4-n-octyl-carbonylamino-salicylate |

TABLE 6

| Recording paper | Whiteness before test | Whiteness after test | | Writing utensils resistance |
|---|---|---|---|---|
| | | Moist heat resistance | Oil resistance | |
| Example | | | | |
| 1 | 82.8 | 81.5 | 81.6 | ○ |
| 2 | 82.8 | 81.6 | 81.5 | ○ |
| 3 | 82.7 | 81.5 | 81.7 | ○ |
| 4 | 82.8 | 81.6 | 81.5 | ○ |
| 5 | 82.7 | 81.5 | 81.5 | ○ |
| 6 | 82.7 | 81.6 | 81.5 | ○ |
| 7 | 82.7 | 81.6 | 81.6 | ○ |
| 8 | 82.8 | 81.5 | 81.7 | ○ |
| 9 | 82.7 | 81.5 | 81.6 | ○ |
| 10 | 82.8 | 81.6 | 81.5 | ○ |
| 11 | 82.7 | 81.5 | 81.7 | ○ |
| 12 | 82.7 | 81.5 | 81.5 | ○ |
| 13 | 82.7 | 81.5 | 81.6 | ○ |
| 14 | 82.7 | 81.5 | 81.6 | ○ |
| 15 | 82.8 | 81.5 | 81.7 | ○ |
| 16 | 82.7 | 81.6 | 81.6 | ○ |
| 17 | 82.8 | 81.5 | 81.7 | ○ |
| 18 | 82.7 | 81.6 | 81.6 | ○ |
| 19 | 82.2 | 81.1 | 81.3 | ○ |
| 20 | 82.2 | 81.0 | 81.2 | ○ |
| 21 | 82.1 | 81.6 | 81.6 | ○ |
| 22 | 82.1 | 81.6 | 81.6 | ○ |
| 23 | 82.0 | 81.4 | 81.4 | ○ |
| 24 | 82.1 | 81.6 | 81.6 | ○ |
| 25 | 82.8 | 81.5 | 81.7 | ○ |
| 26 | 82.7 | 81.5 | 81.6 | ○ |
| 27 | 82.6 | 81.6 | 81.6 | ○ |
| 28 | 82.7 | 81.5 | 81.6 | ○ |
| 29 | 82.6 | 81.5 | 81.6 | ○ |
| 30 | 82.7 | 81.5 | 81.6 | ○ |
| 31 | 82.7 | 81.5 | 81.6 | ○ |
| Comparative Example | | | | |
| 1 | 82.7 | 81.5 | 81.5 | X |
| 2 | 82.6 | 81.3 | 81.3 | X |
| 3 | 75.5 | 58.1 | 7.7 | X |
| 4 | 75.5 | 59.3 | 6.8 | X |
| 5 | 77.5 | 64.2 | 15.2 | X |
| 6 | 80.5 | 79.2 | 78.2 | ○ |
| 7 | 79.7 | 77.3 | 77.3 | ○ |
| 8 | 80.0 | 78.6 | 78.3 | ○ |

TABLE 7

| Recording paper | Residual rate of developed color image (%) | | Writing utensils resistance |
|---|---|---|---|
| | Moist heat resistance | Oil resistance | |
| Example | | | |
| 1 | 98 | 97 | ⊚ |
| 2 | 98 | 98 | ⊚ |
| 3 | 97 | 97 | ⊚ |
| 4 | 99 | 98 | ⊚ |
| 5 | 94 | 93 | ⊚ |
| 6 | 98 | 98 | ⊚ |
| 7 | 99 | 98 | ⊚ |
| 8 | 98 | 98 | ⊚ |
| 9 | 95 | 97 | ⊚ |
| 10 | 93 | 97 | ⊚ |
| 11 | 94 | 95 | ⊚ |
| 12 | 98 | 98 | ⊚ |
| 13 | 99 | 98 | ⊚ |
| 14 | 99 | 98 | ⊚ |
| 15 | 99 | 97 | ⊚ |
| 16 | 98 | 98 | ⊚ |
| 17 | 99 | 98 | ⊚ |
| 18 | 97 | 98 | ⊚ |
| 19 | 96 | 96 | ⊚ |
| 20 | 95 | 94 | ⊚ |
| 21 | 94 | 95 | ⊚ |
| 22 | 94 | 95 | ⊚ |
| 23 | 94 | 95 | ⊚ |
| 24 | 94 | 95 | ⊚ |
| 25 | 99 | 98 | ⊚ |
| 26 | 98 | 97 | ⊚ |
| 27 | 100 | 100 | ⊚ |
| 28 | 95 | 96 | ⊚ |
| 29 | 98 | 98 | ⊚ |
| 30 | 98 | 97 | ⊚ |
| 31 | 98 | 97 | ⊚ |
| Comparative Example | | | |
| 1 | 15 | 10 | X |
| 2 | 11 | 9 | X |
| 3 | 97 | 97 | ○ |
| 4 | 96 | 98 | ○ |
| 5 | 97 | 98 | ○ |
| 6 | 32 | 57 | ○ |
| 7 | 16 | 21 | ○ |
| 8 | 15 | 59 | ○ |

As clearly seen in Table 6 and Table 7, the heat-sensitive recording material of the invention which was prepared by using the salicylic acid derivative represented by the formula (1) and/or the metal salt of said derivative as electron accepting compounds is very excellent in storage stability(moist heat resistance, oil resistance and writing utensils resistance) of the uncolored portion and developed color image as compared with a heat-sensitive recording material prepared by using conventional electron accepting compounds.

EXAMPLE 32

Color forming characteristic test against temperature

Color forming characteristics against temperature of the heat-sensitive recording paper prepared in Examples 2, 3, 4, 6, 7, 8, 9, 24, 27 and 29 were compared with the heat-sensitive recording paper prepared in Comparative Examples 6, 7 and 8.

Color forming characteristic test against temperature was carried out by bringing each heat-sensitive recording paper into contact for 5 seconds with a metal block which was previously heated to a prescribed temperature. The color density of the image thus developed was measured with a Macbeth reflection densitometer. Results are illustrated in Table 8. A larger value indicates higher color density.

TABLE 8

| Recording | Temperature (°C.) | | | | |
|---|---|---|---|---|---|
| paper | 90 | 95 | 100 | 110 | 120 |
| Example | | | | | |
| 2 | 0.07 | 0.23 | 0.55 | 1.15 | 1.33 |
| 3 | 0.06 | 0.20 | 0.61 | 1.27 | 1.32 |
| 4 | 0.07 | 0.24 | 0.55 | 1.20 | 1.33 |
| 6 | 0.06 | 0.20 | 0.57 | 1.15 | 1.34 |
| 7 | 0.06 | 0.20 | 0.65 | 1.27 | 1.32 |
| 8 | 0.07 | 0.20 | 0.63 | 1.19 | 1.32 |
| 9 | 0.06 | 0.22 | 0.62 | 1.12 | 1.33 |
| 24 | 0.06 | 0.22 | 0.59 | 1.14 | 1.32 |
| 27 | 0.07 | 0.24 | 0.58 | 1.18 | 1.32 |
| 29 | 0.06 | 0.21 | 0.56 | 1.22 | 1.33 |
| Comparative Example | | | | | |
| 6 | 0.06 | 0.08 | 0.10 | 0.18 | 0.35 |
| 7 | 0.06 | 0.10 | 0.18 | 0.30 | 0.48 |
| 8 | 0.07 | 0.10 | 0.18 | 0.35 | 0.60 |

As clearly illustrated in Table 8, the heat-sensitive recording material of the invention can quickly develop color image at lower temperatures as compared with heat-sensitive recording materials in which metal salts of conventionally known salicylic acid derivatives having an amide substituent are used as electron accepting compounds, and is suitable for high speed recording.

What is claimed is:

1. A heat-sensitive recording material comprising a color-forming, electron donating compound and an electron accepting compound wherein said electron accepting compound is one or more compound selected from a salicylic acid derivative represented by the formula (1):

wherein $X_1$ and $X_2$ are a hydrogen atom, an alkyl group, an alkoxy group, an aralkyl group, an aryl group or a halogen atom, $Y_1$ and $Y_2$ are an oxygen atom or a sulfur atom, $R_1$ is a hydrogen atom, an alkyl group, an aralkyl group or an aryl group, and $R_2$ is an alkyl group, an alkenyl group, an aralkyl group or an aryl group, and/or a metal salt of said salicylic acid derivative.

2. The heat-sensitive recording material of claim 1 wherein the metal salt is a divalent, trivalent or tetravalent metal salt.

3. The heat-sensitive recording material of claim 1 wherein the metal salt is selected from the group consisting of a zinc, magnesium, calcium, barium, nickel, manganese, cobalt and aluminum salt.

4. The heat-sensitive recording material of claim 1 wherein the metal salt is selected from the group consisting of a zinc, magnesium, nickel, manganese and cobalt salt.

5. The heat-sensitive recording material of claim 1 wherein the metal salt is a zinc salt.

6. The heat-sensitive recording material of claim 1 wherein both of $X_1$ and $X_2$ of the salicylic acid derivative of formula (1) is a hydrogen atom.

7. The heat-sensitive recording material of claim 1 wherein at least one of $Y_1$ and $Y_2$ of the salicylic acid derivative of formula (1) is a sulfur atom.

8. The heat-sensitive recording material of claim 1 wherein $Y_1$ of the salicylic acid derivative of formula (1) is an oxygen atom.

9. The heat-sensitive recording material of claim 1 wherein $R_1$ of the salicylic acid derivative of formula (1) is a hydrogen atom.

10. The heat-sensitive recording material of claim 1 wherein $R_2$ of the salicylic acid derivative of formula (1) is unsubstituted or substituted alkyl of 1 to 24 carbon atoms, unsubstituted or substituted alkenyl of 2 to 24 carbon atoms or unsubstituted or substituted aryl of 6 to 24 carbon atoms.

11. The heat-sensitive recording material of claim 1 wherein the nitrogen atom of the salicylic acid derivative of formula (1) is at the 4 or 5 position.

12. The heat-sensitive recording material of claim 1, wherein the electron accepting compound is a zinc salt of a salicylic acid derivative of formula (1) in which each of $X_1$, $X_2$ and $R_1$ is a hydrogen atom, $R_2$ is unsubstituted or substituted alkyl of 1 to 24 carbon atoms, unsubstituted or substituted alkenyl of 2 to 24 carbon atoms or unsubstituted or substituted aryl of 6 to 24 carbon atoms, $Y_1$ is an oxygen atom and the nitrogen atom is at the 4 or 5 position.

* * * * *